(12) United States Patent
Allen et al.

(10) Patent No.: US 11,974,843 B2
(45) Date of Patent: May 7, 2024

(54) NEAR-INFRARED SPECTROSCOPY SYSTEMS AND METHODS

(71) Applicant: NIRSense LLC, Richmond, VA (US)

(72) Inventors: Jared Dale Allen, Richmond, VA (US); Bretton Robert Goldbach, Richmond, VA (US); Areej Habib, Richmond, VA (US); Jason Michael Strohmaier, Richmond, VA (US); Ryan Casey Boutwell, Richmond, VA (US)

(73) Assignee: NIRSense LLC, Richmond, VA (US)

( * ) Notice: Subject to any disclaimer, the term of this patent is extended or adjusted under 35 U.S.C. 154(b) by 0 days.

(21) Appl. No.: 18/553,543

(22) PCT Filed: Apr. 4, 2022

(86) PCT No.: PCT/US2022/023330
§ 371 (c)(1),
(2) Date: Sep. 29, 2023

(87) PCT Pub. No.: WO2022/212951
PCT Pub. Date: Oct. 6, 2022

(65) Prior Publication Data
US 2024/0081697 A1    Mar. 14, 2024

Related U.S. Application Data

(60) Provisional application No. 63/170,201, filed on Apr. 2, 2021.

(51) Int. Cl.
*A61B 5/1455*      (2006.01)
*A61B 5/00*      (2006.01)

(52) U.S. Cl.
CPC ........ *A61B 5/14551* (2013.01); *A61B 5/6814* (2013.01); *A61B 5/0075* (2013.01);
(Continued)

(58) Field of Classification Search
CPC .............. A61B 5/1455; A61B 5/14551; A61B 5/14552; A61B 5/14553; A61B 5/1495;
(Continued)

(56) References Cited

U.S. PATENT DOCUMENTS

2014/0117256 A1    5/2014   Mueller et al.
2014/0275891 A1    9/2014   Muehlemann et al.
(Continued)

OTHER PUBLICATIONS

International Search Report and Written Opinion dated Jul. 18, 2022, from corresponding International Application No. PCT/US2022/023330.

*Primary Examiner* — Chu Chuan Liu
(74) *Attorney, Agent, or Firm* — Troutman Pepper Hamilton Sanders LLP

(57) ABSTRACT

A near-infrared spectroscopy system comprises a substrate, a light source emitting a set of wavelengths, an optical detector detecting the set of wavelengths, a processor in electronic communication with the light source bank and/or the optical detector, and a memory device in electronic communication with the processor. The light source bank, optical detector, processor, and memory device are mounted on the substrate, and a battery is in electronic communication with at least one of these components. Program instructions direct the processor to calculate an oxygenation level, compare that oxygenation level to a predetermined threshold, and optionally, activate a feedback device. A method of detecting an oxygenation level comprises mounting the system in a wearable article, calculating a baseline oxygenation level, regularly executing the program instructions to calculate the oxygenation level, and activating the feedback device.

19 Claims, 15 Drawing Sheets

(52) U.S. Cl.
CPC . *A61B 2562/0219* (2013.01); *A61B 2562/164* (2013.01); *A61B 2562/185* (2013.01)

(58) Field of Classification Search
CPC ..... A61B 5/6814; A61B 5/681; A61B 5/0075; A61B 2562/164; A61B 2562/185
See application file for complete search history.

(56) References Cited

U.S. PATENT DOCUMENTS

| | | | |
|---|---|---|---|
| 2014/0343383 A1* | 11/2014 | Sato | A61B 5/14551 |
| | | | 600/479 |
| 2016/0098834 A1 | 4/2016 | Eguchi et al. | |
| 2017/0360316 A1* | 12/2017 | Gu | A61B 5/14552 |
| 2018/0042513 A1* | 2/2018 | Connor | A61B 5/14532 |
| 2018/0132766 A1* | 5/2018 | Lee | A61B 5/1455 |
| 2018/0177402 A1 | 6/2018 | Shuler | |
| 2019/0281204 A1 | 9/2019 | Darty et al. | |

* cited by examiner

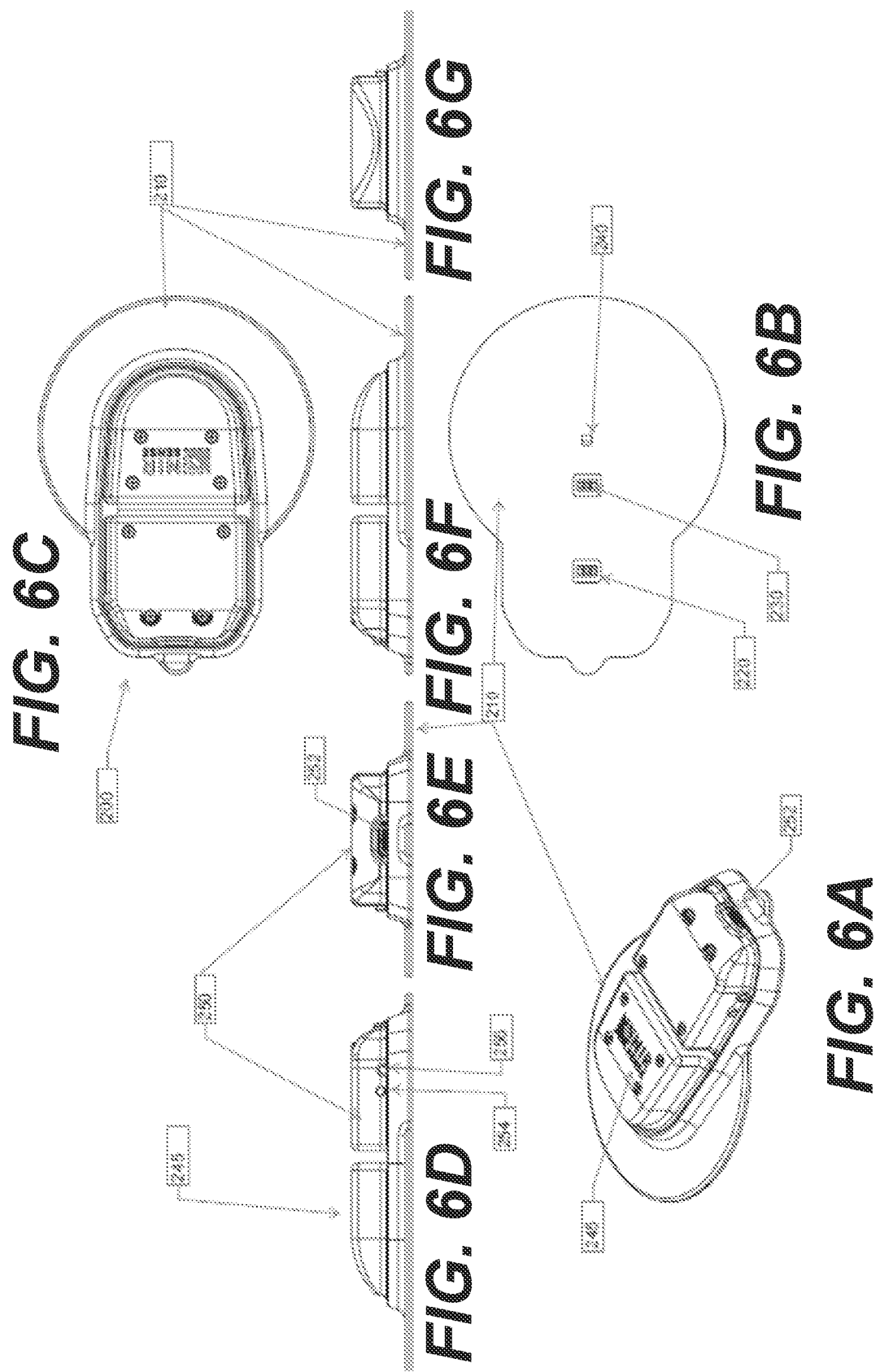

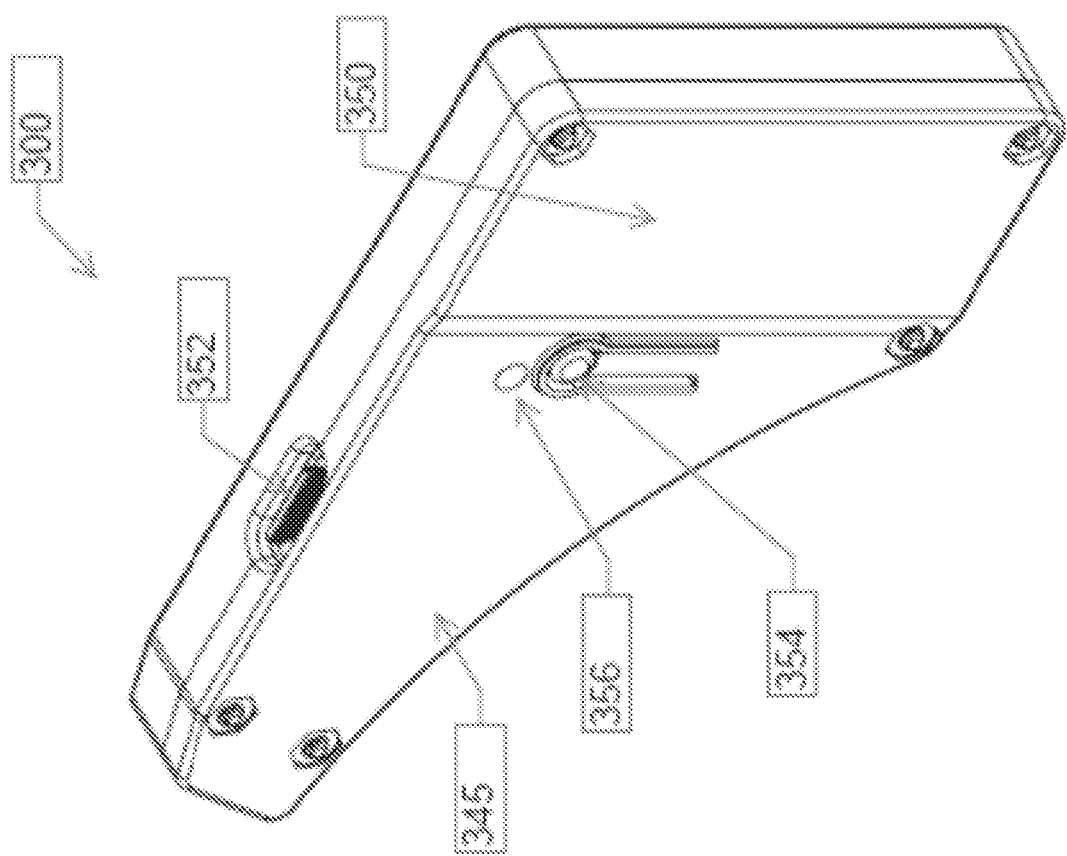

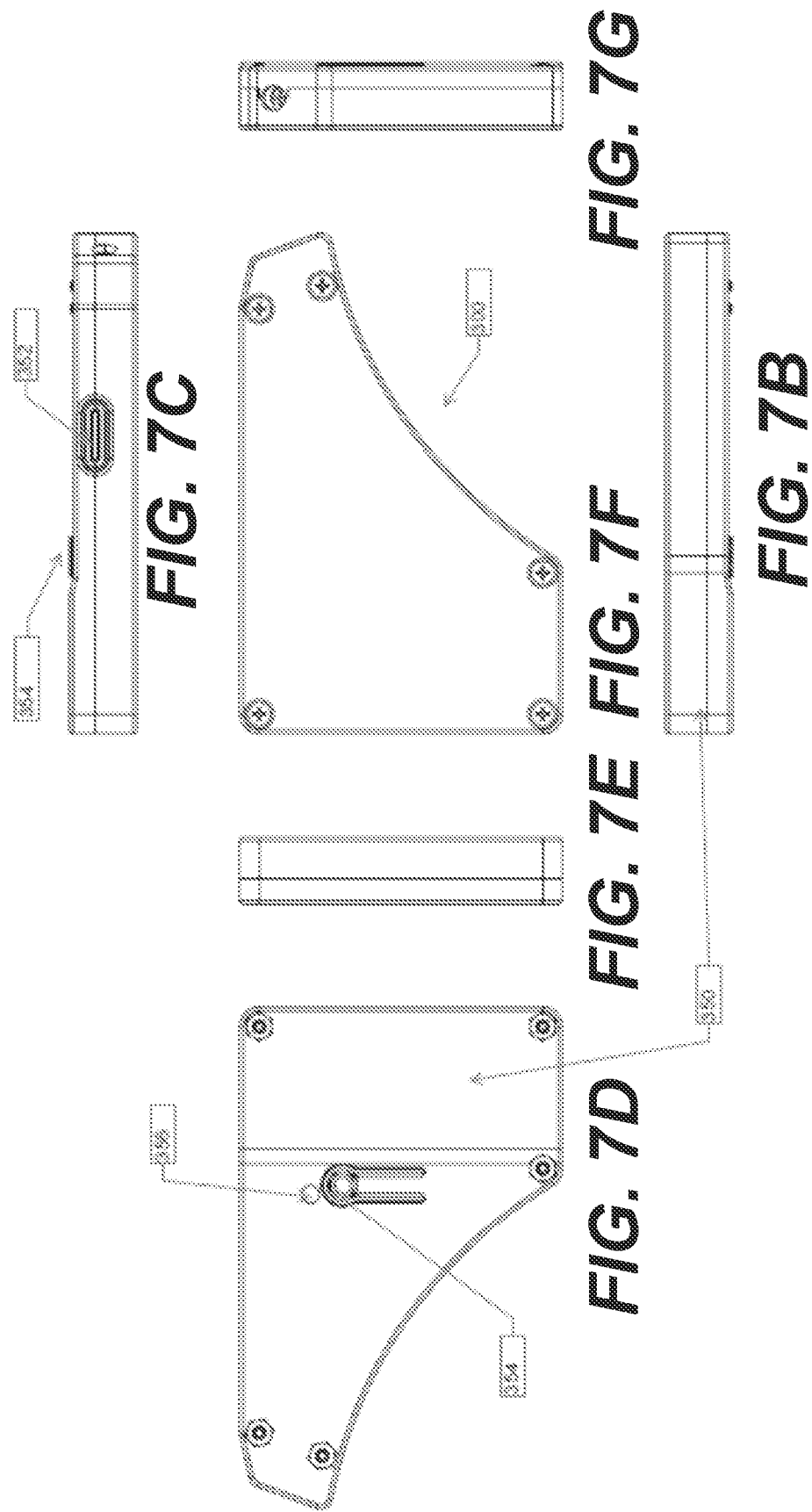

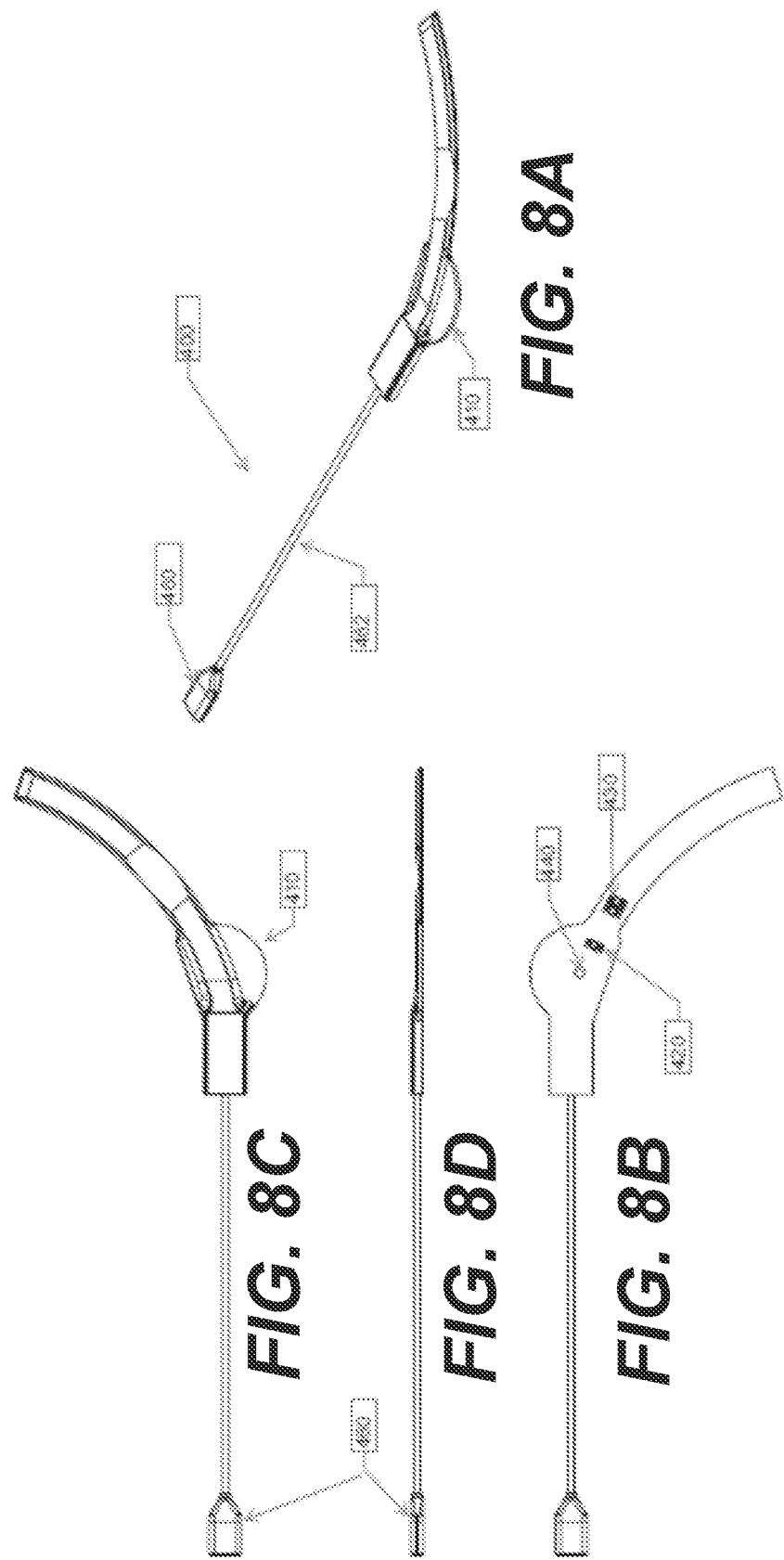

NEAR-INFRARED SPECTROSCOPY SYSTEMS AND METHODS

CROSS REFERENCE TO RELATED APPLICATION

The present application is a U.S. National Phase Application under 35 U.S.C. § 371 of International PCT/US2022/023330 filed Apr. 4, 2022, which claims priority to U.S. Provisional Application Ser. No. 63/170,201 filed Apr. 2, 2021. This application is incorporated herein by reference in its entirety.

TECHNICAL FIELD

The present disclosure relates generally to near-infrared spectroscopy (NIRS) systems and methods. In particular, the present disclosure relates to systems and methods for determining physiological measurements, such as oxygenation levels.

BACKGROUND

Near-infrared spectroscopy (NIRS) devices interrogate biological tissue using a selection of light wavelengths in the red and near-infrared (NIR) region of the electromagnetic spectrum. These wavelengths are particularly well suited for deep light penetration through tissue, versus other wavelengths of light that are scattered or absorbed by confounding factors in the body and thus cannot reach the tissue depth of these red and NIR wavelengths. NIRS devices generally feature at least two wavelengths of light output in this range and at least one detector, and including additional optical elements can allow different depths of sensing or sensing of different tissue characteristics.

Red and near-infrared wavelengths are particularly effective for non-invasively sensing different molecular states of hemoglobin in various body tissues. Unfortunately, existing NIRS devices are typically expensive, large desktop units with disintegrated sensor and processing systems. This lack of portability limits the usefulness of NIRS outside of the surgical suite, laboratory, and research environments. Some portable solutions include a sensor-only patch with wired communication to a separate portable, pocketable, or head-worn processing and communications unit. These changes represent only a nominal improvement, as the processing unit is itself not fully wearable and risks physically detaching the sensor unit through movement or cable weight. These limitations greatly decrease the wearability and utility of such systems. These semi-ambulatory systems are also typically not designed to be used in parallel, where individual NIRS sensor systems work in tandem across the body or across a population to continually sense physiological features at multiple places using a common interface. Non-ambulatory systems can have more sensor inputs, but these are limited by the total number of ports designed into the physical system itself. Therefore, there exists a need for integrated NIRS systems and methods of using those systems to interrogate biological tissue.

SUMMARY

In an embodiment, a near-infrared spectroscopy (NIRS) system may comprise a substrate and a first light source bank capable of emitting a first set of wavelengths of red or near-infrared light. The first light source bank may be mounted on the substrate. In an embodiment, the system may further comprise an optical detector capable of detecting the first set of wavelengths. The optical detector may be mounted on the substrate at a first distance from the first light source bank. In some embodiments, the system may further comprise a processor in electronic communication with at least one of the first light source bank and the optical detector. The processor may be mounted on the substrate. In an embodiment, the system may further comprise a memory device in electronic communication with the processor, wherein the memory device is non-transient. The memory device may be mounted on the substrate. In an embodiment, the system may further comprise a battery in electronic communication with at least one of the first light source bank, the optical detector, the processor, and the memory device.

In some embodiments, the system may further comprise program instructions stored on the memory device that, when executed, direct the processor to: select, based on an input parameter, the first set of wavelengths; select, based on the input parameter, the first distance from the first light source bank; process a signal from the optical detector to calculate an oxygenation level; measure, store, or report, the calculated oxygenation level; and compare the oxygenation level to a predetermined threshold. The program instructions, when executed, may further direct the processor to do at least one of: filter the signal from the optical detector; activate a feedback device when the oxygenation characteristics contain certain signal behaviors, or is different from the predetermined threshold; and store at least one of the signal and the oxygenation level on the memory device; and report the oxygenation characteristics to a remote viewer.

In an embodiment, the system may further comprise a second light source bank capable of emitting a second set of wavelengths of red or near-infrared light, or a second optical detector capable of detecting the first set of wavelengths of red or near-infrared light. The second light source bank or second optical detector may be mounted on the substrate. In an embodiment, the optical detector may be capable of detecting the first set of wavelengths and the second set of wavelengths, or the same first set of wavelengths may be detectable by the first or second optical detector. The optical detector may be mounted on the substrate at the first distance from the first light source bank and at a second distance from the second light source bank, or the first light source bank may be mounted on the substrate and the first and second optical detector may be mounted at a first distance and the second optical detector at a second distance from the first light source bank. The processor may be in electronic communication with at least one of the first light source bank, the second light source bank, the first optical detector, the second optical detector, and the memory device. The program instructions, when executed, may direct the processor to: select, based on the input parameter, at least one of the first set of wavelengths and the second set of wavelengths or at least one of the first optical detector and the second optical detector; and select, based on the input parameter, at least one of the first distance from the first light source bank or first or second optical detector and the second distance from the second light source bank or first or second optical detector. Note that examples of the invention can use one or more light source banks in relation to one or more optical detectors. The examples using multiple light sources and/or detectors need not be directly correlated (e.g. two detectors matched to two light source banks).

In some embodiments, the substrate may be a flexible substrate. In some embodiments, the substrate may comprise at least one rigid portion and at least one flexible portion. In certain embodiments, the substrate may be configured to conform to at least a portion of a mammal's skull. In an embodiment, the system may further comprise a shielding device disposed over at least a portion of the substrate. In some embodiments, the shielding device may be, for example, a metal shield, a layer of reflective paint, a synthetic polymer enclosure, a layer of darkened adhesive, or a combination thereof.

In some embodiments, the battery may be mounted on the substrate, while in other embodiments, the battery may be in electronic communication with at least one of the first light source bank, the second light source bank, the first optical detector, the second optical detector, the processor, and the memory device, via a connector. In some embodiments, a first assembly may comprise the substrate, the first light source bank, the second light source bank, the first optical detector, the second optical detector, the processor, and the memory device. In an embodiment, a second assembly may comprise the battery.

In some embodiments, the predetermined threshold of the oxygenation level is from about 0% oxygen to about 100% oxygen. In an embodiment, the predetermined threshold is from about 50% oxygen to about 100% oxygen.

In some embodiments, the predetermined threshold of oxygenation is a rate of change of % oxygen measured on a scale of 0-100%. In an embodiment, the predetermined rate of change of % oxygen is from about 1% per minute to about 25% per minute.

In some embodiments, the predetermined threshold of oxygenation is a rate of change of % oxygen measured as a relative change from a baseline measurement. In an embodiment, the change from baseline is from about −100% to +300%.

In some embodiments, the feedback device may be, for example, a display, an audible feedback device, a haptic feedback device, a color-based feedback device, a fragrance-based feedback device, a tactile feedback device, or a combination thereof.

In an embodiment, at least one of the optical detectors or at least one of the light source banks may be movably mounted to the substrate. In an embodiment, selecting, based on the input parameter, at least one of the first distance from the first light source bank and the second distance from the second light source bank or the first distance from the first optical detector or the second distance from the second optical detector may further comprise instructing at least one of the light source banks or at least one of the optical detectors to move to at least one of the first distance and the second distance.

In some embodiments, the system may further comprise one or more accelerometers. In an embodiment, each accelerometer is mounted on the substrate. In certain embodiments, each accelerometer may be capable of detecting a change in velocity of up to about 200 G. In an embodiment, the program instructions may further direct the processor to modify the feedback device when the change in velocity exceeds threshold for a predetermined period of time.

In some embodiments, the system may further comprise an inflatable wearable device, and the program instructions may further direct at least one portion of the wearable device to adjust an inflation level of the inflatable wearable device when the oxygenation level is either above or below the predetermined threshold.

In an embodiment, a method of detecting an oxygenation level may comprise mounting the system in a wearable article, placing the wearable article on a body of a user, executing the program instructions for a period of time to calculate an oxygenation level, regularly executing the program instructions to calculate the oxygenation level, and activating the feedback device when the oxygenation level is different from a predetermined threshold.

In an embodiment, the wearable article is inflatable. In some embodiments, the method may further comprise increasing an inflation level of the wearable article when the oxygenation level is below the predetermined threshold. In certain embodiments, the method may further comprise maintaining an inflation level of the wearable article when the oxygenation level is above the predetermined threshold. In some embodiments, the wearable article may comprise, for example, a helmet, a hat, a body suit, a leg covering, a torso covering, an arm covering, a foot covering, or a combination thereof. In an embodiment, the period of time may be determined by the processor based on an input condition. In some embodiments, the period of time may be about 2 minutes. Note that this invention can be used in tandem with other technologies related to exercise and fatigue recovery.

In some embodiments, the system may further comprise an oxygenation device. In an embodiment, the method may further comprise adjusting an output level of the oxygenation device when the oxygenation level is below the predetermined threshold. In some embodiments, the method may further comprise maintaining an output level of the oxygenation device when the oxygenation level is above the predetermined threshold. In some embodiments, the oxygenation device may be, for example, an oxygen tank, an extracorporeal membrane oxygenation (ECMO) device, or a combination thereof.

In some embodiments, the method may comprise activating the feedback device when the oxygenation level is below the predetermined threshold. In certain embodiments, the method may comprise activating the feedback device when the oxygenation level is above the predetermined threshold. In an embodiment, activating the feedback device may provide near-real-time feedback to a user such that the user can make environmental or other adjustments before an oxygenation level deviates significantly from its optimal level. For example, if a user is alerted about a drop in the user's oxygenation level before the user experiences symptoms of that drop, the user may adjust an external oxygen device to increase the flow of oxygen and prevent the onset of symptoms from low oxygenation levels, thus preserving the user's function and competence.

In an embodiment, the system may further comprise an external computing device comprising a memory and a computer processor. The external computing device may be connected to at least a portion of at least one of the processor and the memory device via a connection, wherein at least a portion of the program instructions is also stored on the external computing device. In some embodiments, the connection may be, for example, a wireless connection, a wired connection, a Bluetooth connection, a near-field communication (NFC) connection, a radio frequency identification (RFID) connection, or a combination thereof.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings:

FIG. 6A depicts a top, rear left perspective view of another example in accordance with the present disclosure.

FIG. 6B depicts a bottom view of the example of FIG. 6A in accordance with the present disclosure.

FIG. 6C depicts a top view of the example of FIG. 6A in accordance with the present disclosure.

FIG. 6D depicts a left side view of the example of FIG. 6A in accordance with the present disclosure.

FIG. 6E depicts a back view of the example of FIG. 6A in accordance with the present disclosure.

FIG. 6F depicts a right side view of the example of FIG. 6A in accordance with the present disclosure.

FIG. 6G depicts a front view of the example of FIG. 6A in accordance with the present disclosure.

FIG. 7A depicts a top, rear left perspective view of a further example in accordance with the present disclosure.

FIG. 7B depicts a bottom view of the example of FIG. 7A in accordance with the present disclosure.

FIG. 7C depicts a top view of the example of FIG. 7A in accordance with the present disclosure.

FIG. 7D depicts a left side view of the example of FIG. 7A in accordance with the present disclosure.

FIG. 7E depicts a back view of the example of FIG. 7A in accordance with the present disclosure.

FIG. 7F depicts a right side view of the example of FIG. 7A in accordance with the present disclosure.

FIG. 7G depicts a front view of the example of FIG. 7A in accordance with the present disclosure.

FIG. 8A depicts a top, rear left perspective view of a further example of a patch assembly in accordance with the present disclosure.

FIG. 8B depicts a bottom view of the example of FIG. 8A in accordance with the present disclosure.

FIG. 8C depicts a top view of the example of FIG. 8A in accordance with the present disclosure.

FIG. 8D depicts a left side view of the example of FIG. 8A in accordance with the present disclosure.

DETAILED DESCRIPTION

Figure 1:
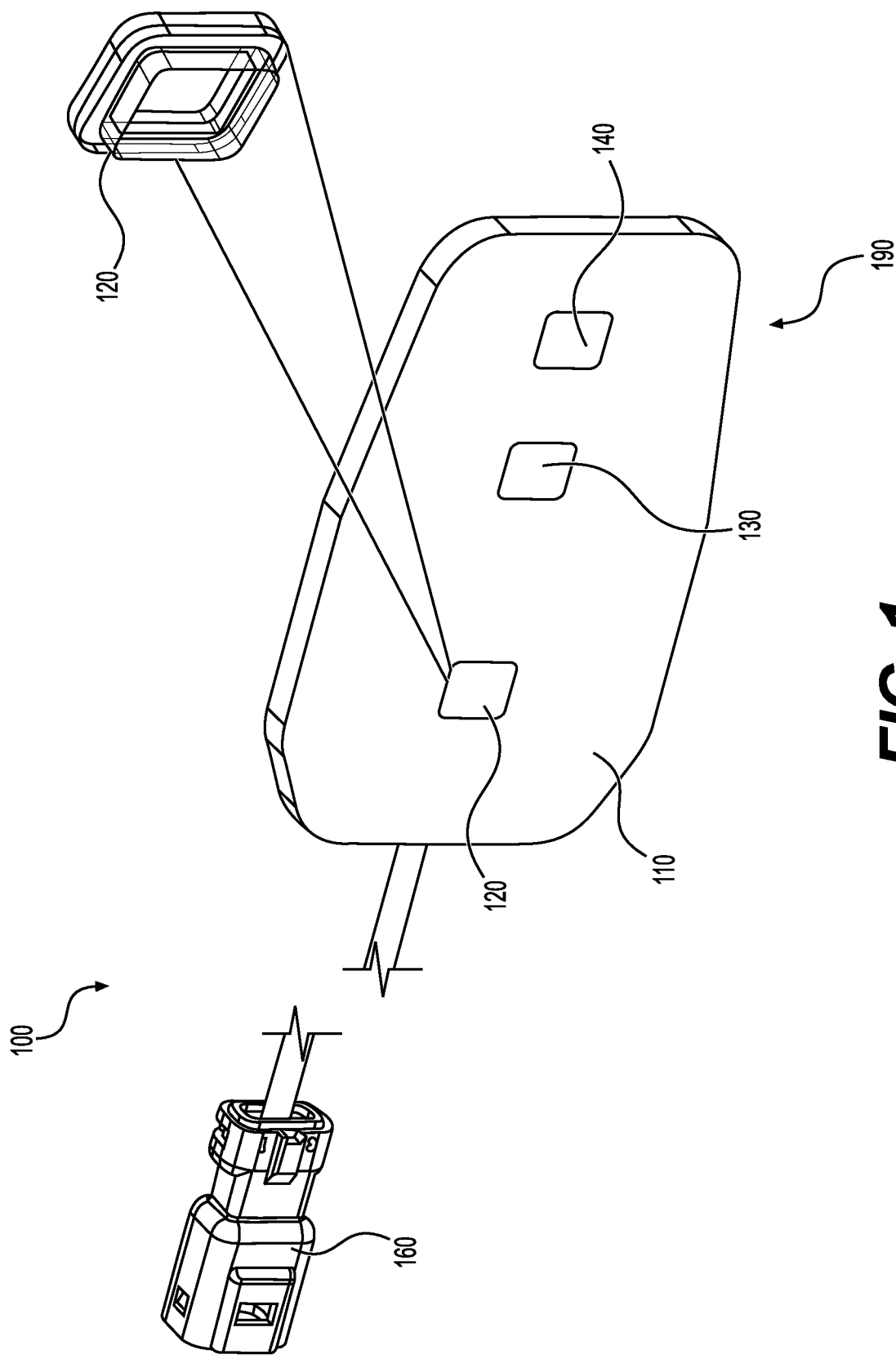
FIG. 1 depicts an embodiment of a near-infrared spectroscopy (NIRS) system, in accordance with the present disclosure.

This disclosure is not limited to the particular systems, devices, and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "fiber" is a reference to one or more fibers and equivalents thereof known to those skilled in the art, and so forth.

As used herein, the term "about" means plus or minus 10% of the numerical value of the number with which it is being used. For example, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term comprising is used as the transition phrase, such embodiments can also be envisioned with replacement of the term "comprising" with the terms "consisting of" or "consisting essentially of."

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two components," without other modifiers, means at least two components, or two or more components). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

Furthermore, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Near-infrared spectroscopy (NIRS) devices interrogate biological tissue using a selection of light wavelengths in the red and near-infrared (NIR) region of the electromagnetic spectrum. These wavelengths are particularly well suited for deep light penetration through tissue, versus lower wavelengths of light that are scattered or absorbed by confounding factors in the body and thus cannot reach the tissue depth of these red and NIR wavelengths. NIRS devices generally feature at minimum two wavelengths of light output in this range and at least one detector, and including additional optical elements can allow different depths of sensing.

Red and near-infrared wavelengths are particularly effective for non-invasively sensing different molecular states of hemoglobin in various body tissues. Hemoglobin is a strong absorber of light in the middle of the visible light spectrum but has a low optical extinction coefficient within the higher wavelengths of the visible range. Within the NIR wavelengths, for hemoglobin's oxygenation states, deoxy- and oxyhemoglobin's absorption spectra cross at an isosbestic point near 805 nm, allowing NIRS systems to differentiate oxygenation states of hemoglobin using light sources above and below this frequency. With this differentiation, NIRS can be used for a variety of sensing mechanisms related to the body's circulatory and other functional systems.

Hemoglobin also allows for binding of ligands other than oxygen. These other molecular states of hemoglobin, such as carboxyhemoglobin and methemoglobin, have unique optical absorption characteristics in the NIR range. Investigating these molecular states can elucidate competitive binding and indicate histologic changes in tissue oxygenation such as tissue poisoning. Hemoglobin has a competitive binding efficiency for many molecules, such as carbon monoxide (CO), cyanide ($CN^-$), sulfur monoxide (SO), sulfide ($S^{2-}$), and others in these groups. Nitric oxide (NO) also binds to hemoglobin and can be detected optically. Investigating the NIR spectra of these additional bound states of hemoglobin can indicate tissue status and toxicity by inhibiting oxygen binding as well as enable sophisticated physiological monitoring of body systems.

NIRS systems may calculate oxygenation levels using the modified Beer-Lambert law (mBLL), which only requires one bank of light sources. Using the mBLL offers the translation of raw optical signals into actionable oxygenation details. Alternatively, NIRS systems may employ spatially resolved spectroscopy (SRS), which can use both short- and long-distance measurements. Separately, short channel information can be subtracted from long channel information to more accurately isolate, for example, brain activity and the contributions from internal (e.g., cerebral) vasculature and external (e.g., skin) vasculature.

Unfortunately, existing NIRS devices are typically expensive, large desktop units with disintegrated sensor and processing systems. This lack of portability limits the usefulness of NIRS outside of the surgical suite, laboratory, and research environments. Even in such controlled environments, these devices sometimes fail because they are difficult to integrate into a user's system when the planned testing involves any form of motion.

Some portable solutions include a sensor-only patch with wired communication to a separate portable, pocketable, or head-worn processing and communications unit. These changes represent only a nominal improvement, as the processing unit is itself not fully wearable and risks physically detaching the sensor unit through movement or cable weight. These limitations greatly decrease the wearability and utility of such systems. These semi-ambulatory systems are also typically not designed to be used in parallel, where individual NIRS sensor systems work in tandem across the body or across a population to continually sense physiological features at multiple places using a common interface. Non-ambulatory systems can have more sensor inputs, but these are limited by the total number of ports designed into the physical system itself. Therefore, there exists a need for integrated NIRS systems and methods of using those systems to interrogate biological tissue.

In an embodiment, a near-infrared spectroscopy (NIRS) system may comprise a substrate. In some embodiments, the substrate may be a flexible substrate. In some embodiments, the substrate may comprise at least one rigid portion and at least one flexible portion. In certain embodiments, the substrate may be a rigid substrate. In some embodiments, the substrate may comprise one or more materials selected from the group consisting of silicone, nylon, a bioinert polymer, a biocompatible polymer, a woven or nonwoven textile, an adhesive film, or a combination thereof. In some embodiments, the substrate and any components mounted onto the substrate may be configured to provide mechanical flexibility, allowing the system to conform to and/or adhere to a body surface. In certain embodiments, the substrate may be configured to conform to at least a portion of a mammal's skull.

In an embodiment, the system may further comprise a shielding device disposed over at least a portion of the substrate. In some embodiments, the shielding device may be, for example, a metal shield, a layer of reflective paint, a synthetic polymer enclosure, a layer of darkened adhesive, or a combination thereof. In some embodiments, the shielding device may serve to shield one or more portions of the substrate from one or more electromagnetic fields, one or more ambient light sources, or a combination thereof.

In some embodiments, the system may further comprise a housing disposed over at least a portion of the substrate. In an embodiment, the housing may be a metal housing a plastic housing, a ceramic housing, or any other type of housing known in the art. In certain embodiments, the housing may serve to protect one or more portions of the system from dirt, dust, water, moisture, physical force, impact, crushing, and the like.

In some embodiments, the system may further comprise a first light source bank. In some embodiments, the first light source bank may comprise a single light source. In other embodiments, the first light source bank may comprise multiple light sources, such as 2 light sources, 3 light sources, 4 light sources, 5 light sources, and so on. In some embodiments, each light source may comprise one or more light emitting diode (LEDs). In some embodiments, each light source may comprise a single tunable light source such as a broadband LED coupled with a miniature monochromator or other tool for selecting a portion of the light source's emitted wavelengths. In an embodiment, the light source bank may include a light source driver capable of selecting between the different light sources or selecting the wavelength from a tunable light source. In some embodiments, the first light source bank may be mounted on the substrate.

In an embodiment, the first light source bank may be capable of emitting a first set of wavelengths of red or near-infrared light. In some embodiments, each light source within the first light source bank may be capable of independently emitting a wavelength. The first set of wavelengths may comprise 1 wavelength, 2 wavelengths, 3 wavelengths, 4 wavelengths, 5 wavelengths, 6 wavelengths, 7 wavelengths, 8 wavelengths, 9 wavelengths, 10 wavelengths, or any other number of wavelengths known in the art. In an embodiment, each wavelength within the first set of wavelengths may independently be from about 660 nm to about 940 nm. Each wavelength may be, for example, about 660 nm, about 665 nm, about 670 nm, about 675 nm, about 680 nm, about 685 nm, about 690 nm, about 695 nm, about 700 nm, about 705 nm, about 710 nm, about 715 nm, about 720 nm, about 725 nm, about 730 nm, about 735 nm, about 740 nm, about 745 nm, about 750 nm, about 755 nm, about 760 nm, about 765 nm, about 770 nm, about 775 nm, about 780 nm, about 785 nm, about 790 nm, about 795 nm, about 800 nm, about 805 nm, about 810 nm, about 815 nm, about 820 nm, about 825 nm, about 830 nm, about 835 nm, about 840 nm, about 845 nm, about 850 nm, about 855 nm, about 860 nm, about 865 nm, about 870 nm, about 875 nm, about 880 nm, about 885 nm, about 890 nm, about 895 nm, about 900 nm, about 905 nm, about 910 nm, about 915 nm, about 920 nm, about 925 nm, about 930 nm, about 935 nm, about 940 nm, or any range between any two of these values, including endpoints. In an embodiment, each wavelength within the first set of wavelengths may be greater than about 805 nm. In some embodiments, the average of the first set of wavelengths may be greater than about 805 nm. In certain embodiments, the first set of wavelengths may include three individual wavelengths to interrogate the targeted tissue: one in the NIR region below the 805 nm isosbestic point, and two above the isosbestic point.

In an embodiment, the system may further comprise a second light source bank. In some embodiments, the second light source bank may comprise a single light source. In other embodiments, the second light source bank may comprise multiple light sources, such as 2 light sources, 3 light sources, 4 light sources, 5 light sources, and so on. In some embodiments, each light source may comprise one or more light emitting diode (LEDs). In an embodiment, the second light source bank may be mounted on the substrate. In some embodiments, each light source may comprise a single tunable light source such as a broadband LED coupled with a miniature monochromator. In an embodiment, the light source bank may include a light source driver capable of selecting between the different light sources or selecting the wavelength from a tunable light source. In some embodiments, the first light source bank may be mounted on the substrate.

In some embodiments, the second light source bank may be capable of emitting a second set of wavelengths of red or near-infrared light. In some embodiments, each light source within the second light source bank may be capable of independently emitting a wavelength. The second set of wavelengths may comprise 1 wavelength, 2 wavelengths, 3 wavelengths, 4 wavelengths, 5 wavelengths, 6 wavelengths, 7 wavelengths, 8 wavelengths, 9 wavelengths, 10 wavelengths, or any other number of wavelengths known in the art. In an embodiment, each wavelength within the first second set of wavelengths may independently be from about 660 nm to about 940 nm. Each wavelength may be, for example, about 660 nm, about 665 nm, about 670 nm, about 675 nm, about 680 nm, about 685 nm, about 690 nm, about 695 nm, about 700 nm, about 705 nm, about 710 nm, about 715 nm, about 720 nm, about 725 nm, about 730 nm, about 735 nm, about 740 nm, about 745 nm, about 750 nm, about 755 nm, about 760 nm, about 765 nm, about 770 nm, about 775 nm, about 780 nm, about 785 nm, about 790 nm, about 795 nm, about 800 nm, about 805 nm, about 810 nm, about 815 nm, about 820 nm, about 825 nm, about 830 nm, about 835 nm, about 840 nm, about 845 nm, about 850 nm, about 855 nm, about 860 nm, about 865 nm, about 870 nm, about 875 nm, about 880 nm, about 885 nm, about 890 nm, about 895 nm, about 900 nm, about 905 nm, about 910 nm, about 915 nm, about 920 nm, about 925 nm, about 930 nm, about 935 nm, about 940 nm, or any range between any two of these values, including endpoints. In an embodiment, each wavelength within the second set of wavelengths may be less than about 805 nm. In some embodiments, the average of the second set of wavelengths may be less than about 805 nm. In certain embodiments, the first set of wavelengths may include three individual wavelengths to interrogate the targeted tissue: one in the NIR region below the 805 nm isosbestic point, and two above the isosbestic point.

In an embodiment, the system may further comprise an optical detector. In an embodiment, the optical detector may be configured to detect backscattered light from the first light source bank, the second light source bank, or a combination thereof, as the backscattered light travels through tissue. In some embodiments, the optical detector may comprise a single optical detector. In other embodiments, the optical detector may comprise multiple optical detectors, such as 2 optical detectors, 3 optical detectors, 4 optical detectors, 5 optical detectors, and so on. In some embodiments, the optical detector may be capable of detecting the first set of wavelengths, as described herein. In an embodiment, the optical detector may be capable of detecting the first set of wavelengths and the second set of wavelengths, as described herein.

In an embodiment, the optical detector may be mounted on the substrate. In certain embodiments, the optical detector may be mounted on the substrate at a first distance from the first light source bank. In an embodiment, the first distance may be from about 0.8 cm to about 4.5 cm. The first distance may be, for example, about 0.8 cm, about 0.9 cm, about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, about 2.1 cm, about 2.2 cm, about 2.3 cm, about 2.4 cm, about 2.5 cm, about 2.6 cm, about 2.7 cm, about 2.8 cm, about 2.9 cm, about 3.0 cm, about 3.1 cm, about 3.2 cm, about 3.3 cm, about 3.4 cm, about 3.5 cm, about 3.6 cm, about 3.7 cm, about 3.8 cm, about 3.9 cm, about 4.0 cm, about 4.1 cm, about 4.2 cm, about 4.3 cm, about 4.4 cm, about 4.5 cm, or any range between any two of these values, including endpoints. In an embodiment, the first distance may be about 4 cm.

In some embodiments, the optical detector may be mounted on the substrate at a second distance from the second light source bank. In an embodiment, the second distance may be from about 0.8 cm to about 4.5 cm. The second distance may be, for example, about 0.8 cm, about 0.9 cm, about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, about 2.1 cm, about 2.2 cm, about 2.3 cm, about 2.4 cm, about 2.5 cm, about 2.6 cm, about 2.7 cm, about 2.8 cm, about 2.9 cm, about 3.0 cm, about 3.1 cm, about 3.2 cm, about 3.3 cm, about 3.4 cm, about 3.5 cm, about 3.6 cm, about 3.7 cm, about 3.8 cm, about 3.9 cm, about 4.0 cm, about 4.1 cm, about 4.2 cm, about 4.3 cm, about 4.4 cm, about 4.5 cm, or any range between any two of these values, including endpoints. In an embodiment, the second distance may be about 1.5 cm.

In some embodiments, the system may further comprise a processor. In an embodiment, the processor may be in electronic communication with at least one of the first light source bank and the optical detector. In some embodiments, processor may be in electronic communication with at least one of the first light source bank, the second light source bank, the optical detector, the processor, and the memory device. In some embodiments, the processor may be mounted on the substrate.

In an embodiment, the system may further comprise a memory device, as described herein. In some embodiments, the memory device may be in electronic communication with the processor. In an embodiment, the memory device may be non-transient. In some embodiments, the memory device may be mounted on the substrate. The memory device may comprise a memory device known in the art, as described herein.

In an embodiment, the system may further comprise a battery. The battery may be in electronic communication with one or more of the system's other components, as described herein. In an embodiment, when the battery is in electronic communication with (i.e., electrically connected to and capable of communicating with) one or more of the system's other components, the battery may transfer power between itself and the one or more other components, thereby powering the one or more other components while also ensuring that the battery itself does not overheat or is not otherwise compromised.

In some embodiments, the battery may be in electronic communication with at least one of the first light source bank, the optical detector, the processor, and the memory device. In some embodiments, the battery may be mounted on the substrate. In other embodiments, the battery may be in electronic communication with at least one of the first light source bank, the second light source bank, the optical detector, the processor, and the memory device, via a connector. In some embodiments, the battery may be charged using a wireless power receiver module. In certain embodiments, a battery can be charged using on-board power harvesting sources such as photovoltaic cells, thermoelectric generators, or piezoelectric power harvesting capable of harvesting power from motion of the wearer.

In some embodiments, a first assembly may comprise the substrate, the first light source bank, the second light source bank, the optical detector, the processor, and the memory device. In an embodiment, a second assembly may comprise the battery. In certain embodiments, the battery may be mounted to the substrate, such that the NIRS system is contained within a single assembly rather than multiple assemblies.

In some embodiments, the system may further comprise program instructions stored on the memory device. In an embodiment, the program instructions may, when executed, direct the processor to perform various functions. In some embodiments, the functions may include selecting, based on an input parameter, the first set of wavelengths, as described herein. In certain embodiments, the functions may include selecting, based on the input parameter, at least one of the first set of wavelengths and the second set of wavelengths, as described herein. The input parameter may include, for example, a temperature, a lighting condition, a characteristic of the interrogated layer as described herein, a velocity, an acceleration, a change in acceleration, a pressure, a change in pressure, a volume, a change in volume, a measurement made, recorded, or calculated by the system, a communication from another device or system, or a combination thereof.

In certain embodiments, the functions may also include selecting, based on the input parameter, the first distance from the first light source bank, as described herein. In some embodiments, the functions may also include selecting, based on the input parameter, at least one of the first distance from the first light source bank and the second distance from the second light source bank, as described herein.

In some embodiments, the functions may also include processing a signal from the optical detector to calculate an oxygenation level, as described herein. For example, in embodiments wherein the system is used for cerebral oxygenation detection, the interrogated layer as described herein may include the cerebral matter, the meninges, the skull, and/or the scalp. In such embodiments, the first light source bank, for example, may emit light that passes through the cerebrum, cerebrospinal fluid, skull, adipose layer, interstitium, skin, and other intermediate layers; the second light source bank may emit light through those tissues that don't include the cerebrum. The step of processing the signal from the optical detector may include isolating the oxygenation within the cerebral tissue by mathematically filtering out these other sources by comparing the first and second light signatures. In embodiments wherein the system is used for somatic tissue oxygenation detection, the interrogated layer may include muscle, organ, or other tissue beneath an adipose layer, interstitium, and skin or connective tissue within the body. The system may similarly isolate the oxygenation status of this tissue without the impact of confounding factors closer to the skin or organ surface.

In certain embodiments, the functions may further include comparing the oxygenation level to a predetermined threshold level or other characteristic of changing oxygenation including for example percent oxygenation change per unit of time. In an embodiment, the predetermined threshold or characteristic may comprise one or more predetermined thresholds or characteristics, or a set of predetermined thresholds or characteristics. In certain embodiments, the predetermined threshold may be determined or calculated while the system is being used, and in other embodiments the predetermined threshold may be set in the program instructions before the system is used. In other words, the threshold is "predetermined" in that it is identified before the comparison is completed, but need not be predetermined before the system is used or before the program instructions are executed.

In some embodiments, the predetermined threshold of the oxygenation level is from about 0% oxygen to about 100% oxygen. The predetermined threshold of the oxygenation level may be, for example, about 0% oxygen, about 5% oxygen, about 10% oxygen, about 15% oxygen, about 20% oxygen, about 25% oxygen, about 30% oxygen, about 35% oxygen, about 40% oxygen, about 45% oxygen, about 50% oxygen, about 55% oxygen, about 60% oxygen, about 65% oxygen, about 70% oxygen, about 75% oxygen, about 80% oxygen, about 85% oxygen, about 90% oxygen, about 95% oxygen, about 100% oxygen, or any range between any two of these values, including endpoints. In an embodiment, the predetermined threshold is from about 50% oxygen to about 100% oxygen.

In some embodiments, the program instructions, when executed, may direct the processor to do at least one additional step. These additional steps may include, for example, filtering the signal from the optical detector; activating a feedback device when the oxygenation level is below the predetermined threshold; and storing at least one of the signal and the oxygenation level on the memory device.

As noted above, the additional steps may optionally include filtering the signal from the optical detector. For example, filtering motion, an ambient light condition, an ambient sound condition, or a combination thereof may improve the signal-to-noise ratio (SNR) of the signal from the optical detector. The additional steps may also optionally include smoothing the signal from the optical detector.

As noted above, the additional steps may optionally include activating a feedback device when the oxygenation level is below the predetermined threshold. In some embodiments, the feedback device may be, for example, a display, an audible feedback device, a haptic feedback device, a color-based feedback device, a fragrance-based feedback device, a tactile feedback device, or a combination thereof. The feedback device may be configured to alert a user and/or a monitor to adjust an oxygenation device, a garment, and the like to optimize the user's oxygenation level, for example. As noted above, the additional steps may also optionally include storing at least one of the signal and the oxygenation level on the memory device.

In some embodiments, the optical detector may be fixedly mounted to the substrate. In certain embodiments, the optical detector may be movably mounted to the substrate. The movable mounting may include mechanical and/or electrical mounting. In an embodiment, selecting, based on the input parameter, at least one of the first distance from the first light source bank and the second distance from the second light source bank may further comprise instructing the optical detector to move to at least one of the first distance and the second distance.

In some embodiments, the system may further comprise one or more accelerometers. In an embodiment, each accelerometer is mounted on the substrate. In certain embodiments, each accelerometer may be capable of detecting a change in velocity in a low range of up to about 16 G, and/or in a high range of up to about 200 G. Each accelerometer may be capable of detecting a change in velocity in a range of up to, for example, about 4G, about 8G, about 12G, about 16G, about 20G, about 30G, about 40G, about 50G, about 60G, about 70G, about 80G, about 90G, about 100G, about 110G, about 120G, about 130G, about 140G, about 150G, about 160G, about 170G, about 180G, about 190G, about 200G, or any range between any two of these values, including endpoints.

In an embodiment, the program instructions may further direct the processor to modify the feedback device when the change in velocity differs from a threshold for a predetermined period of time. When a user is subjected to a rapid change in velocity as detected by the accelerometer, for example, a sudden but temporary change in the user's oxygenation level may be expected, such that activating the feedback device would unnecessarily alert the user to the temporary exchange, falsely causing alarm. Deactivating the feedback device under such conditions may prevent such false alarms.

In some embodiments, the system may further comprise an inflatable wearable device or article, as described herein. In certain embodiments, the program instructions may further direct at least one portion of the wearable device or article to either adjust or maintain an inflation level of the inflatable wearable device when the oxygenation level is either above or below the predetermined threshold. For example, increasing the inflation level of the inflatable wearable device when the oxygenation level is below the predetermined threshold may compress one or more tissues of the user, thereby raising the oxygenation level back to a preferred range. Similarly, decreasing the inflation level of the inflatable wearable device when the oxygenation level is above the predetermined threshold may allow for conservation of oxygen from an external oxygen source, especially in settings in which external oxygen is limited.

In an embodiment, the system may further comprise an associated charging base station, a smartphone, a computer, or additional NIRS systems that are working in parallel (networked or individually) across separate areas of the user's or wearer's body. To aid in data correction to account for motion and signal variability, the system may use a motion sensing module to interpret and correct data as it is collected. This motion sensing module may also contribute unique physiological information to further enhance the quality and scope of the system's monitoring capabilities.

In some embodiments, the system may be a fully sealed unit that has no electrical or mechanical ports, emitting/detecting only light from optically transparent windows in the substrate, and encased in a protective medium such as medical-grade silicon, molded plastic, or similar encapsulating material. The components of the system may be covered by a transparent media such as epoxy that seamlessly integrates with the rest of the system enclosure to maintain water- and dust-tightness for the system while allowing backscattered light through the enclosure.

FIG. 1 depicts an embodiment of a near-infrared spectroscopy (NIRS) system 100. As shown in FIG. 1, the system 100 comprises a substrate 110, a first light source bank 120 mounted on the substrate 110, and a second light source bank 130 mounted on the substrate 110. The system further comprises an optical detector 140 mounted on the substrate 110 at the first distance from the first light source bank 120 and at a second distance from the second light source bank 130. The system also comprises a processor (not shown) in electronic communication with at least one of the first light source bank 120, the second light source bank 130, and the optical detector 140, the processor (not shown) mounted on the substrate 110. The system further comprises a memory device (not shown) in electronic communication with the processor (not shown), the memory device (not shown) mounted on the substrate 110. FIG. 1 includes a first assembly 190 that comprises the substrate 110, the first light source bank 120, the second light source bank 130, the optical detector 140, the processor (not shown), and the memory device (not shown).

Figure 2:
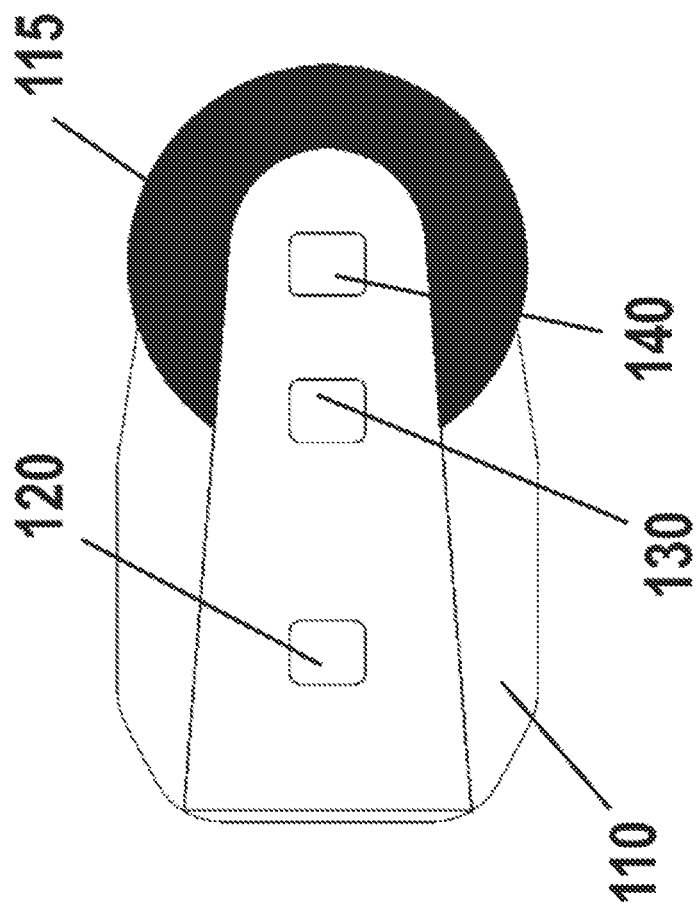
FIG. 2 depicts an embodiment of a near-infrared spectroscopy (NIRS) system having a shielding device, in accordance with the present disclosure.

FIG. 2 depicts an embodiment of a system as described herein, comprising a substrate 110, a first light source bank 120 mounted on the substrate 110, a second light source bank 130 mounted on the substrate 110, and a shielding device 115 disposed over at least a portion of the substrate 110. In the embodiment depicted in FIG. 2, the shielding device 115 comprises at least one layer of darkened adhesive.

Figure 3A:
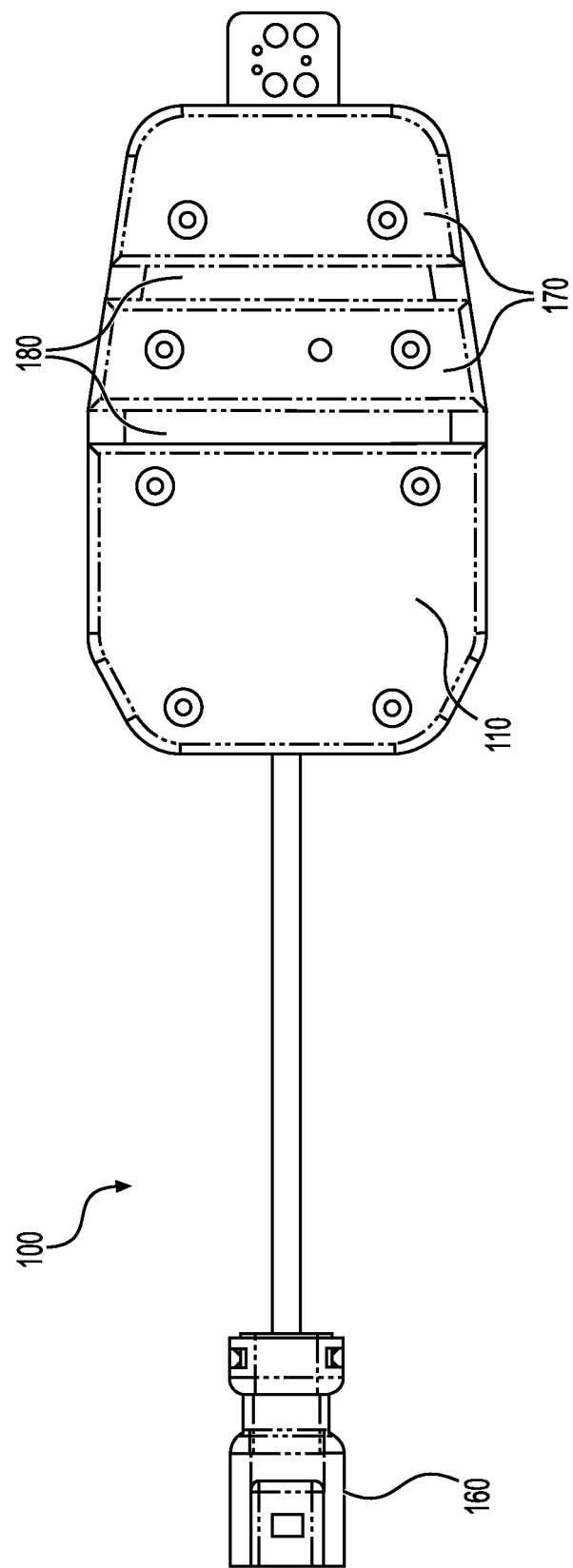
FIG. 3A depicts a top view of an embodiment of a near-infrared spectroscopy (NIRS) system, in accordance with the present disclosure.
Figure 3B:
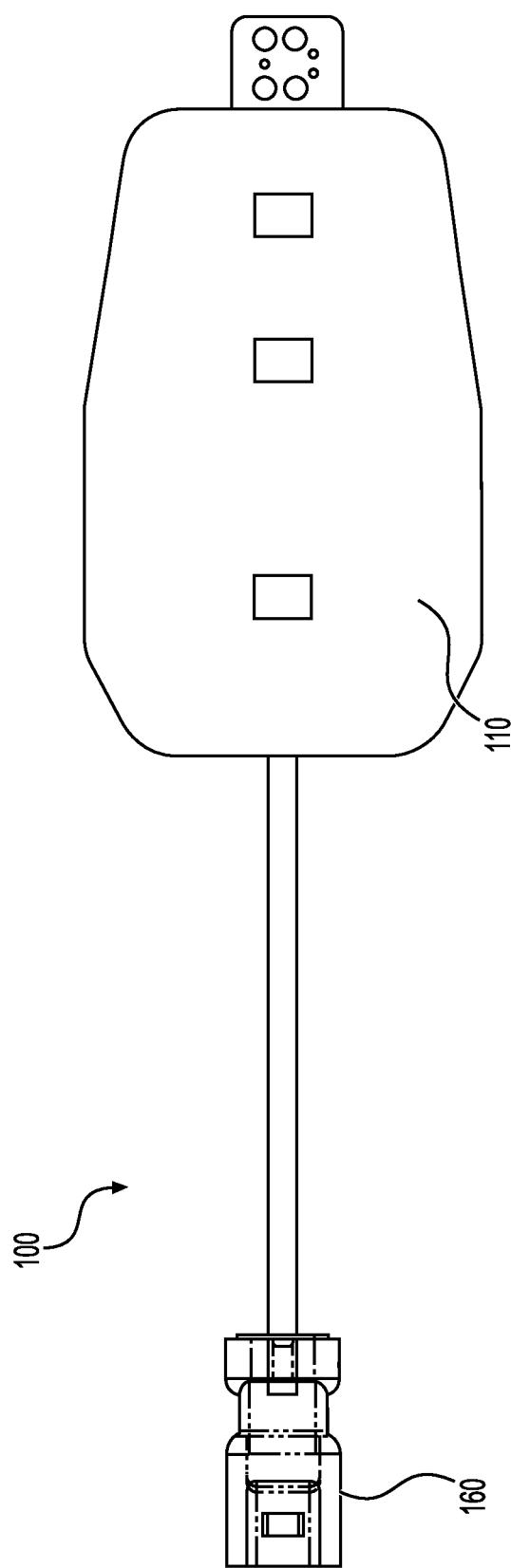
FIG. 3B depicts a bottom view of the near-infrared spectroscopy (NIRS) system of FIG. 4A, in accordance with the present disclosure.
Figure 3C:
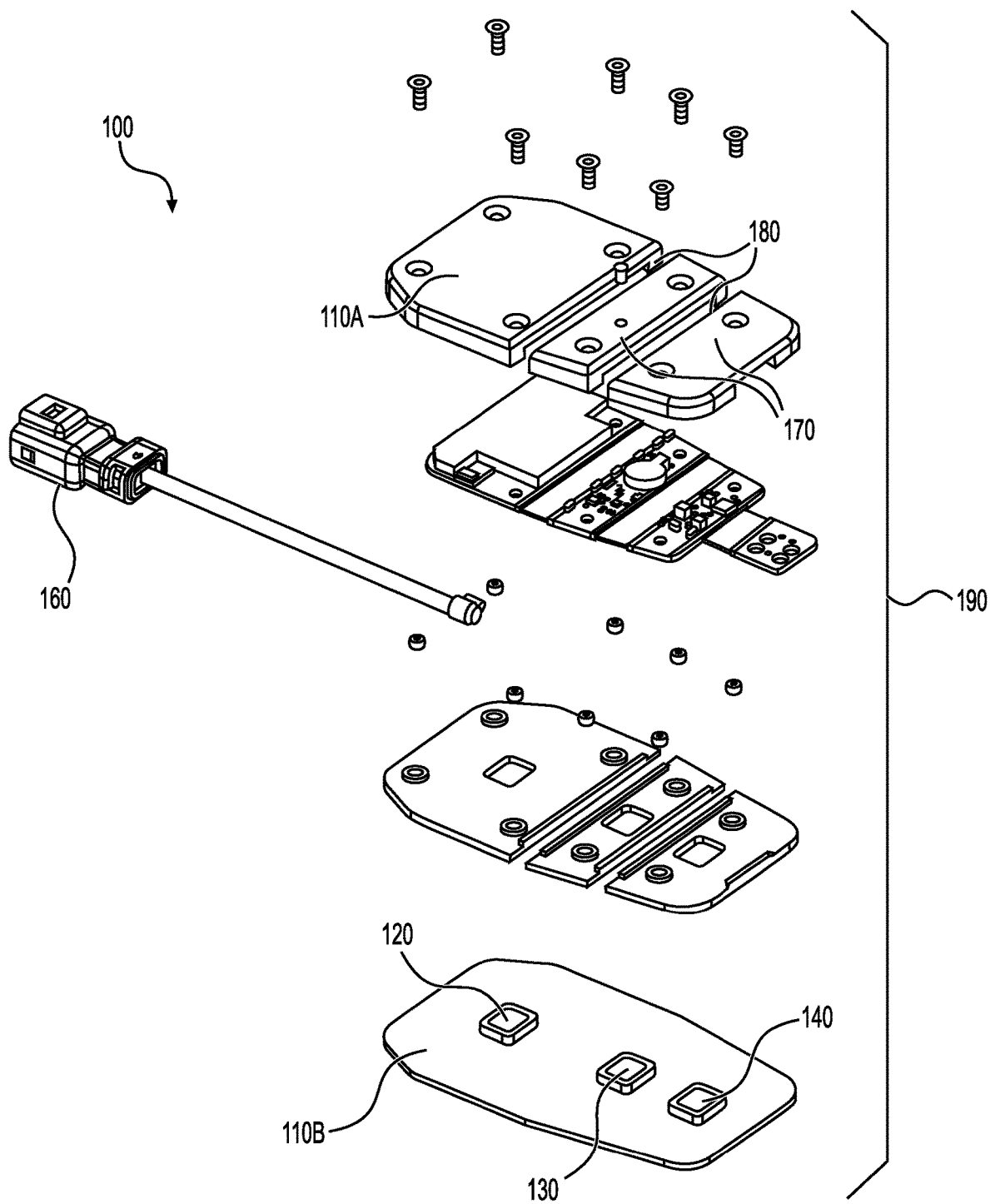
FIG. 3C depicts an exploded view of the near-infrared spectroscopy (NIRS) system of FIG. 4A, in accordance with the present disclosure.

FIG. 3A, FIG. 3B, and FIG. 3C depict an embodiment of a near-infrared spectroscopy (NIRS) system 100 that includes a connector 160 and substrate 110 having at least one rigid portion 170 and at least one flexible portion 180. FIG. 3A shows a top view of the system 100, and FIG. 3B shows a bottom view of the system 100. FIG. 3C shows an exploded view of the system 100, comprising a substrate 110A/110B, a first light source bank 120 mounted on the substrate 110B, a second light source bank 130 mounted on the substrate 110B, and an optical detector 140 mounted on the substrate 110B at the first distance from the first light source bank 120 and at a second distance from the second light source bank 130. The system 100 also comprises a processor in electronic communication with at least one of the first light source bank 120, the second light source bank 130, and the optical detector 140. The system 100 further comprises a memory device in electronic communication with the processor. The system 100 comprises a first assembly 190 that comprises the substrate 110A/110B, the first light source bank 120, the second light source bank 130, the optical detector 140, the processor, and the memory device. At least a portion of the first assembly 190 is in electronic communication with a battery (not shown) via a connector 160.

Figure 4A:
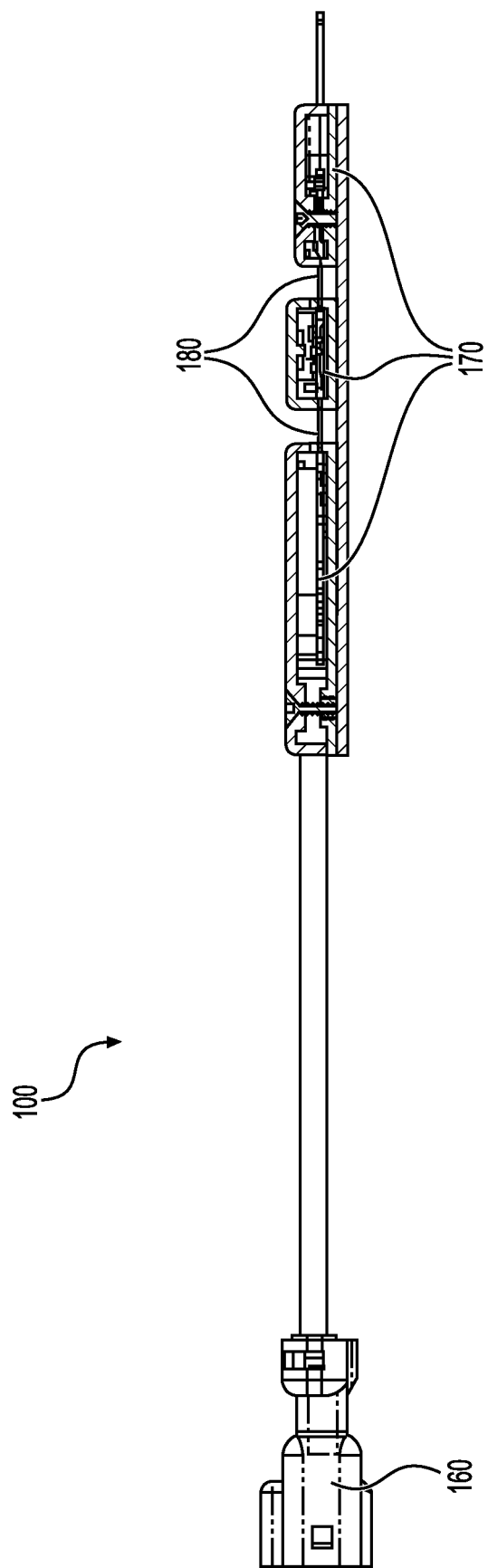
FIG. 4A depicts a cross-sectional view of an embodiment of a near-infrared spectroscopy (NIRS) system, in accordance with the present disclosure.
Figure 4B:
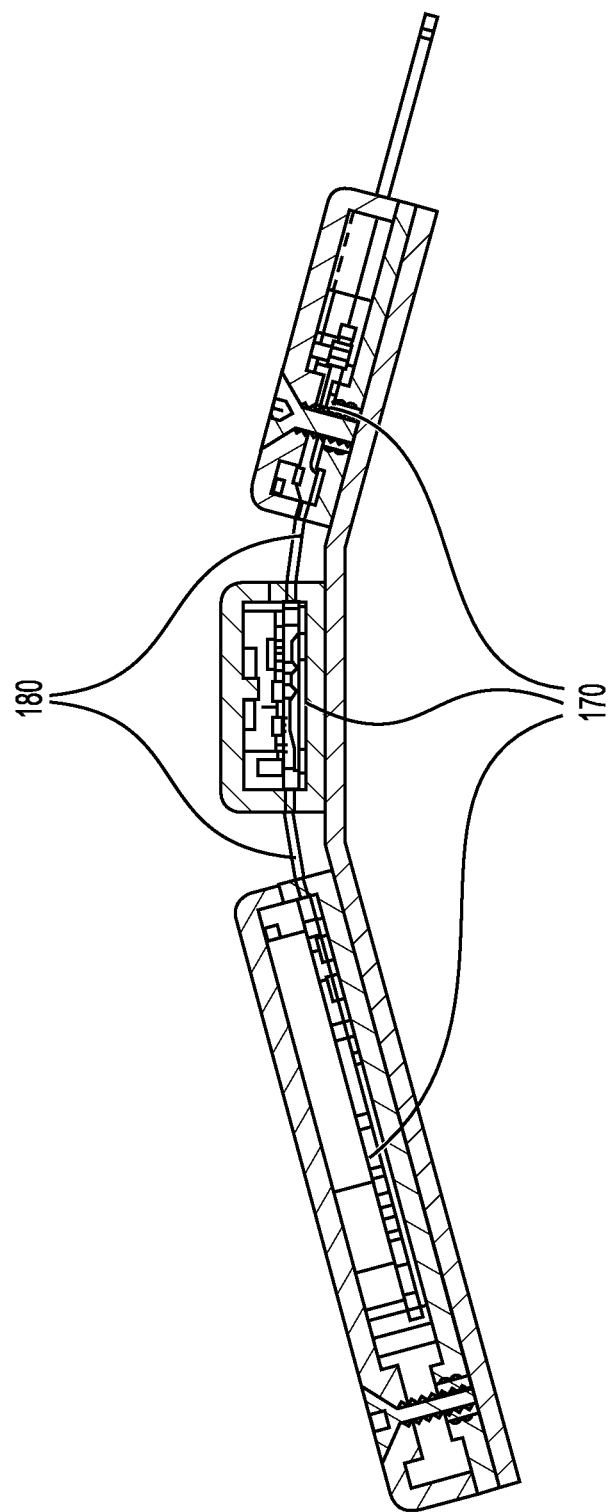
FIG. 4B depicts a cross-sectional view of the near-infrared spectroscopy (NIRS) system of FIG. 5A in a flexed position, in accordance with the present disclosure.

FIG. 4A and FIG. 4B depict an embodiment of a near-infrared spectroscopy (NIRS) system 100 that includes a connector 160 and substrate 110 having at least one rigid portion 170 and at least one flexible portion 180. FIG. 4A shows a cross-section of the system 100, having three rigid portions 170, two flexible portions 180, and a connector 160. FIG. 4B shows a cross-section of the system 100 having three rigid portions 170 and two flexible portions 180 shown in a flexed position. In some embodiments, the flexed position may be useful for accommodating or conforming to a curved portion of a wearer's body, as described herein.

FIG. 5A, FIG. 5B, FIG. 5C, and FIG. 5D depict a second assembly 195 that comprises a battery 150. In the embodiments shown in, for example, FIG. 1 and FIG. 5A, the battery 150 (contained within the second assembly 195) is in electronic communication with at least one of the first light source bank 120, the second light source bank 130, the optical detector 140, the processor (not shown), and the memory device (not shown), via a connector 160.

Figure 5A:
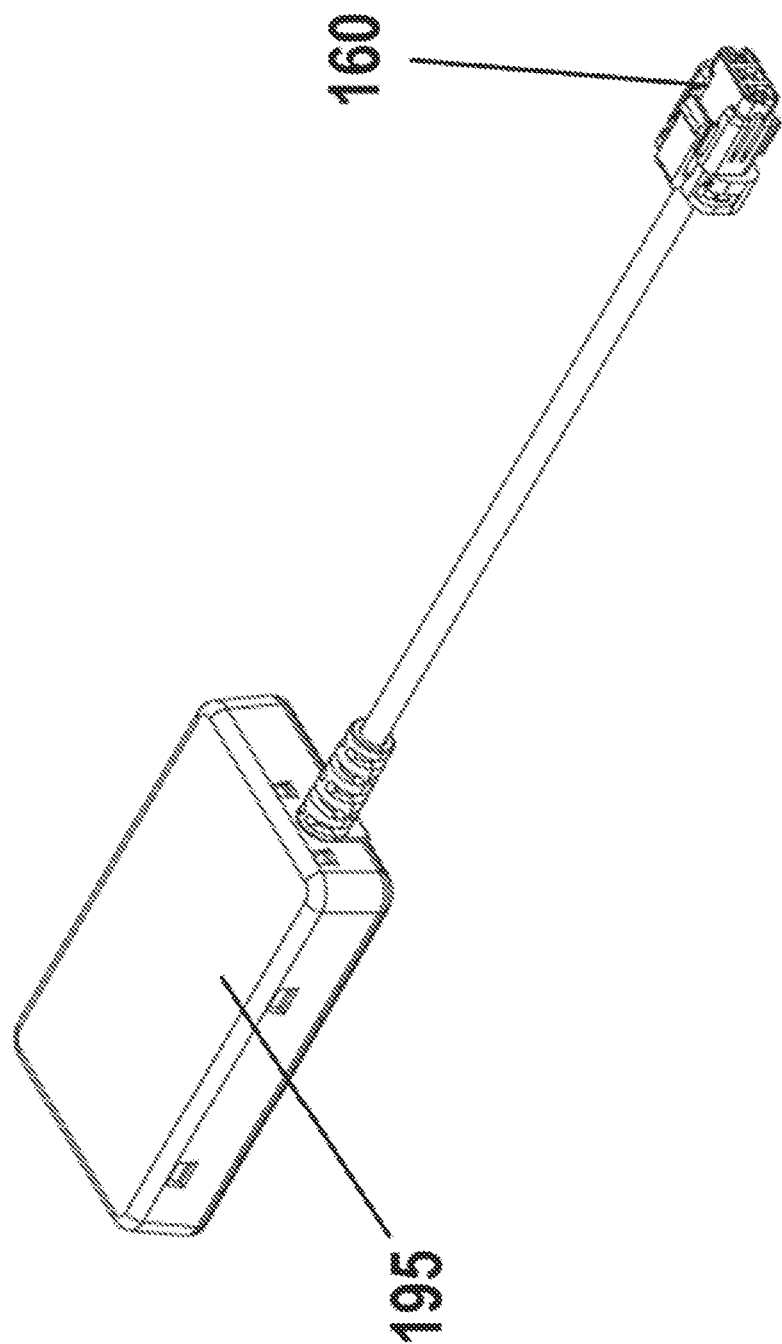
FIG. 5A depicts an embodiment of an assembly comprising a battery, in accordance with the present disclosure.
Figure 5B:
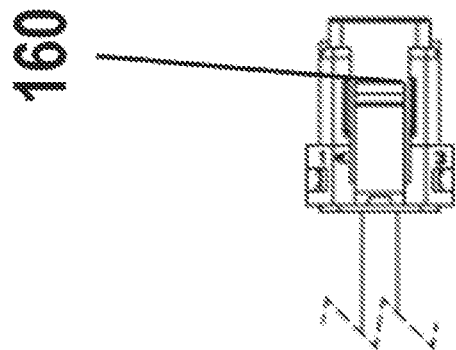
FIG. 5B depicts a top view of the assembly of FIG. 5A, in accordance with the present disclosure.
Figure 5B:
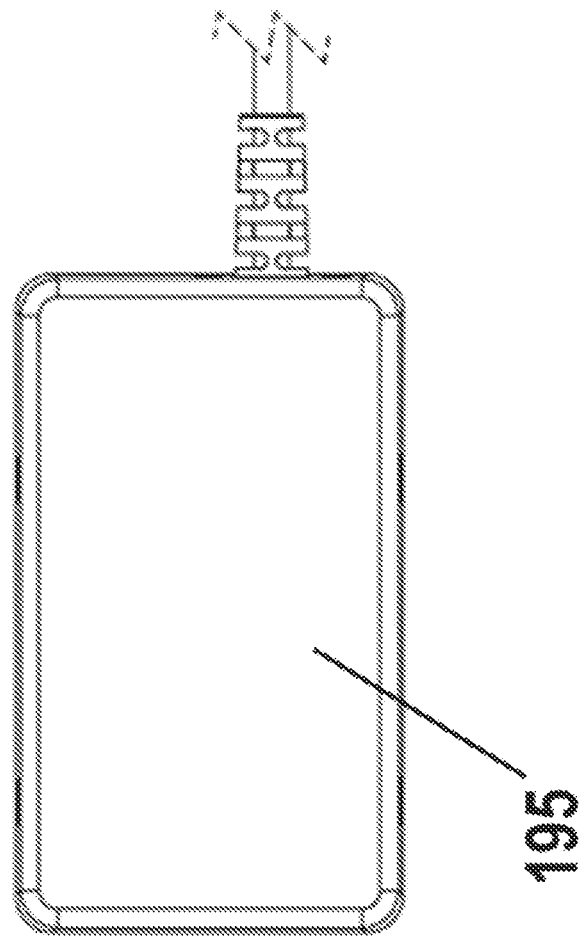
Figure 5C:
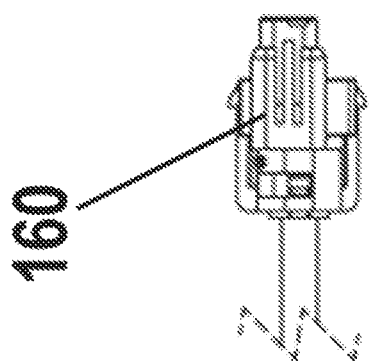
FIG. 5C depicts a side view of the assembly of FIG. 5A, in accordance with the present disclosure.
Figure 5C:
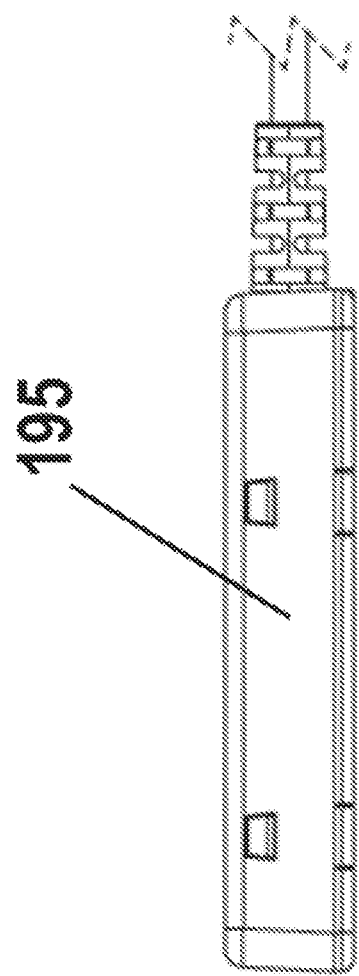
Figure 5D:
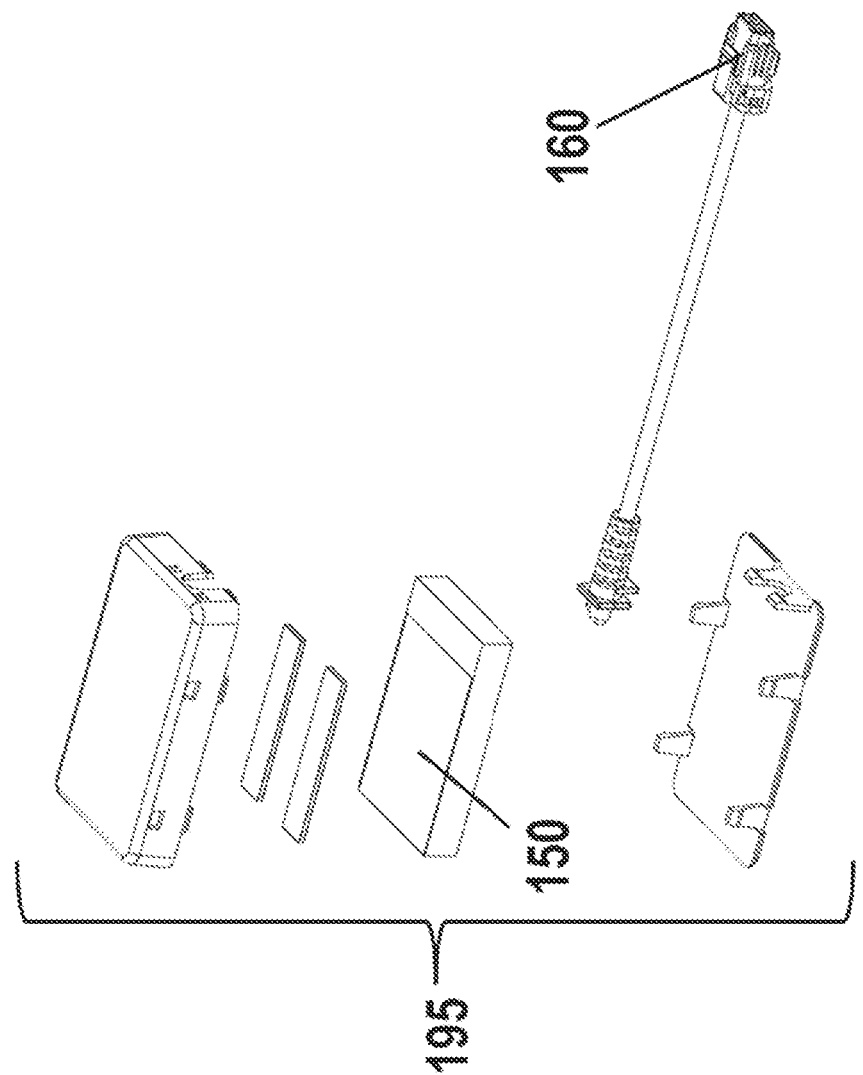
FIG. 5D depicts an exploded view of the assembly of FIG. 5A, in accordance with the present disclosure.

FIG. 5D depicts an exploded view of the second assembly 195 comprising the battery 150, and the connector 160 by which the battery 195 is in electronic communication with, referring back to FIG. 1, at least one of the first light source bank 120, the second light source bank 130, the optical detector 140, the processor (not shown), and the memory device (not shown).

FIGS. 6A-6G depict an example of a near-infrared spectroscopy (NIRS) system 200 with an integrated patient substrate 210. As shown in FIG. 6A, the system 200 comprises a substrate 210, a first light source bank 220 mounted on the substrate 210, and a second light source bank 230 mounted on the substrate 210. The system further comprises an optical detector 240 mounted on the substrate 210 at the first distance from the first light source bank 220 and at a second distance from the second light source bank 230. The system also comprises a processor (not shown) in electronic communication with at least one of the first light source bank 220, the second light source bank 230, and the optical detector 240, the processor (not shown) mounted on the substrate 210. The system further comprises a memory device (not shown) in electronic communication with the processor (not shown), the memory device (not shown) mounted on the substrate 210. FIGS. 6A-6G include an integrated system 200 that comprises the substrate 210, the first light source bank 220, the second light source bank 230, the optical detector 240, the battery 250, the processor (not shown), and the memory device (not shown). A portion of the of the non-battery components can be housed in a logic housing 245 with others housed beneath the battery 250.

FIGS. 6A-6G also illustrate a data/power port 252. The port 252 can be a USB-C port or similar interface. At a minimum, the port 252 allows the battery to be charged. The port 252 can also allow for the transfer of data to and from the memory. An on/off switch 254 along with a power LED 256 allow a user to power on and off the system 200. This example integrates all of the components described above into a single device.

FIGS. 7A-7G illustrate another example of a power/logic module 300 of the present invention. Again, a power/data port 352 accompanies the 354 on/off switch and a power indication LED 356. The form factor of the battery 350, logic housing 345, and other non-sensory components (processor, memory, etc.) allow this module 300 to sit inside of a helmet without impacting wearer comfort.

FIGS. 8A-8D illustrates a patch assembly 400 which communicates with a power/logic module 300 or similar device 100. The connection from the patch assembly 400 to the module 100, 300 is connector 460 which interfaces with port 352. Cable 362 links the connector 460 with the first and second light source banks 420, 430. The light is detected by optical detector 440. The detection and data storage and retrieval are similar to the examples above. The form factor of patch assemble 400 allows it to be mounted near the edge of a helmet while maintaining close contact to the cerebral monitoring area desired.

In some embodiments, the systems described herein are configured to function in a closed loop—that is, to communicate with each other and/or with other devices or systems without the need for external (e.g., user) input. In an embodiment, data from the systems described herein may inform an autonomous artificial intelligence (AI) system such that the autonomous AI system may itself adjust its operation according to the data.

In an embodiment, a method of detecting an oxygenation level may comprise mounting the NIRS system described herein in a wearable article. In some embodiments, the wearable article may comprise, for example, a helmet, a hat, a headband, a shirt, an arm sleeve, an arm band, a wrist band, a body suit, a pair of pants, a leg sleeve, a leg band, a leg covering, a torso covering, a torso band, an arm covering, a foot covering, a shoe, a foot band, an ankle band, or a combination thereof.

In some embodiments, the method of detecting the oxygenation level may further comprise placing the wearable article on a body of a user. The body of the user may include an interrogated layer (i.e., one or more biological tissues in which the system is configured to detect the oxygenation level).

In some embodiments, the method of detecting the oxygenation level may further comprise executing the program instructions for a period of time to calculate a baseline oxygenation level. Distinct from calibrating, calculating a baseline oxygen level may allow the system to provide user-specific feedback by comparing the oxygenation level to an individual user's baseline oxygenation level in a particular environment or set of circumstances, for more valuable feedback during use of the system. In an embodiment, the period of time may occur in a different environmental setting or at a different time than the comparison environment or time. In an embodiment, the period of time may be determined by the processor based on an input condition. In some embodiments, the period of time may be from about 1 second to about 10 minutes. The period of time may be, for example, about 1 second, about 2 seconds, about 3 seconds, about 4 seconds, 5 seconds, about 10 seconds, about 15 seconds, about 30 seconds, about 1 minute, about 1.5 minutes, about 2 minutes, about 2.5 minutes, about 3 minutes, about 3.5 minutes, about 4 minutes, about 4.5 minutes, about 5 minutes, about 5.5 minutes, about 6 minutes, about 6.5 minutes, about 7 minutes, about 7.5 minutes, about 8 minutes, about 8.5 minutes, about 9 minutes, about 9.5 minutes, about 10 minutes, or any range between any two of these values, including endpoints. In an embodiment, the period of time is about 2 minutes.

In some embodiments, the method may further comprise comparing the baseline oxygenation level to a first predetermined threshold or change characteristic. In an embodiment, the first predetermined threshold may comprise a lower predetermined threshold or change characteristic. In another embodiment, the first predetermined threshold may comprise an upper predetermined threshold or change characteristic. In some embodiments, the method may further comprise comparing the baseline oxygenation level to a second predetermined threshold or change characteristic. In an embodiment, the second predetermined threshold may comprise a lower predetermined threshold or change characteristic. In another embodiment, the second predetermined threshold may comprise an upper predetermined threshold or change characteristic.

In an embodiment, the lower predetermined threshold may be from about 0% below the baseline oxygenation level to about 25% below the baseline oxygenation level. The lower predetermined threshold may be, for example, about 0% below the baseline oxygenation level, about 5% below the baseline oxygenation level, about 10% below the baseline oxygenation level, about 15% below the baseline oxygenation level, about 20% below the baseline oxygenation level, about 25% below the baseline oxygenation level, or any range between any two of these values, including endpoints. In an embodiment, the lower predetermined threshold may be from about 10% below the baseline oxygenation level to about 25% below the baseline oxygenation level.

In an embodiment, the upper predetermined threshold may be from about 0% above the baseline oxygenation level to about 25% above the baseline oxygenation level. The upper predetermined threshold may be, for example, about 0% above the baseline oxygenation level, about 5% above the baseline oxygenation level, about 10% above the baseline oxygenation level, about 15% above the baseline oxygenation level, about 20% above the baseline oxygenation level, about 25% above the baseline oxygenation level, or any range between any two of these values, including endpoints. In an embodiment, the upper predetermined threshold may be from about 10% above the baseline oxygenation level to about 25% above the baseline oxygenation level.

In some embodiments, the method of detecting the oxygenation level may further comprise regularly executing the program instructions to calculate the oxygenation level. In an embodiment, regularly executing may comprise autonomously executing the program instruction at a set interval of time, and/or when a set of conditions are met.

In some embodiments, the method of detecting the oxygenation level may further comprise activating the feedback device, as described herein, when the oxygenation level is different from the predetermined threshold. In some embodiments, the method may comprise activating the feedback device when the oxygenation level is below the predetermined threshold. In certain embodiments, the method may comprise activating the feedback device when the oxygenation level is above the predetermined threshold.

In an embodiment, the wearable article may be inflatable. In some embodiments, the method may further comprise increasing an inflation level of the wearable article when the oxygenation level is below the predetermined threshold. In certain embodiments, the method may further comprise maintaining an inflation level of the wearable article when the oxygenation level is above the predetermined threshold.

In some embodiments, the system may further comprise an oxygenation device. In some embodiments, the oxygenation device may be, for example, an oxygen tank, an extracorporeal membrane oxygenation (ECMO) device, or a combination thereof.

In an embodiment, the method may further comprise adjusting an output level of the oxygenation device when the oxygenation level is below the predetermined threshold. In some embodiments, the method may further comprise maintaining an output level of the oxygenation device when the oxygenation level is above the predetermined threshold.

In an embodiment, the system may further comprise an external computing device comprising a memory and a computer processor. The external computing device may be connected to at least a portion of at least one of the processor and the memory device via a connection, wherein at least a portion of the program instructions is also stored on the external computing device. In some embodiments, the connection may be, for example, a wireless connection, a wired connection, a Bluetooth connection, a near-field communication (NFC) connection, a radio frequency identification (RFID) connection, or a combination thereof. In some embodiments, data processing and real-time feedback may occur within the components onboard the substrate, or offboard through communication with the external computing device. The external computing device may comprise, for example, a smartphone, a charging or communications base station, a display screen, a tablet, a computer, a mobile or web-based application, or another device.

In some embodiments, the systems disclosed herein can be networked for concurrent monitoring of different physiological conditions of a user, the same or different physiological conditions at different locations on the body of a user, one or more physiological conditions of a group of wearers in a population, or a combination thereof.

Although some of the processing systems described herein can be embodied in software or code executed by general purpose hardware as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc.

In some embodiments, the near-infrared spectroscopy systems and methods described herein include independent wireless devices communicating oxygenation information about different areas of tissue (ex. the brain) simultaneously. In some embodiments, the functional near-infrared spectroscopy systems and methods described herein include scanning a single device over different areas of the body and continuously imaging tissue; changing methods based on determined tissue state or changes in patient condition.

In some embodiments, the functional near-infrared spectroscopy systems and methods described herein include two or more independent NIRS systems that can simultaneously interrogate multiple areas of cerebral and somatic tissue to interrelate physiological status (for example, tissue oxygenation) in each area. These areas may have significantly different oxygenation signatures at any given time and simultaneously sampling these is particularly important to understand situations of local or central fatigue or recovery onset by the user. Simultaneous imaging of different body systems can also elucidate generalized physiological condition, for instance indicating systemic response to exogenous conditions such as carbon monoxide poisoning or endogenous conditions such as hemorrhage. The independently sampled processed data from each area of the body may then send signals to a user interface if a specific tissue level, condition, or status is reached, or stream data to the external processing module for real-time interpretation, or both.

In some embodiments, the functional near-infrared spectroscopy systems and methods described herein include independent wireless devices communicating multi-point physiological information (ex. oxygenation) about the brain and body simultaneously.

In some embodiments, the functional near-infrared spectroscopy systems and methods described herein include multiple NIRS systems that can be worn by multiple different individuals whose data is integrated to form a comprehensive image of a group of individuals' health. This integration can be simultaneous for co-located users or asynchronous for disparate groups, or another combination. For example, comparing real-time physiological monitoring across multiple individuals can enable population monitoring and a more holistic image of group performance and wellness. Such continuous imaging can identify early threats or enhancements and increase risk or opportunity for better group performance and outcome.

As an example, a set of n NIRS systems are placed on the heads or bodies of n users. Each system is as described herein and includes an LED user interface light indicating a green/yellow/red indication of tissue health. Based on individual physiology of the n users, the n NIRS systems monitor users in this cohort for cerebral or somatic oxygenation depending on the individual user's needs. In an example, one system in the user cohort begins sending abnormal backscattered light signals back to the external processing unit indicating the onset of change in the target population, and providing earlier notification from earlier surveillance.

In some embodiments, the near-infrared spectroscopy systems and methods described herein include monitoring population health through a network of individual users' NIRS systems. In some embodiments, this can enable broader decision making and earlier insight into performance degradations or risks from proximity to decompensating neighbors. For example, the monitored conditions can include pre-symptomatic detection of infection, or fatigue, or environmental exposure and the implementation of remedial strategies to optimize outcome.

Where any component discussed herein is implemented in the form of software, any one of a number of programming languages may be employed such as, for example, C, C++, C #, Objective C, Java®, JavaScript®, Perl, PHP, Visual Basic®, Python®, Ruby, Flash®, or other programming languages. A number of software components are stored in the memory and are executable by the processor. In this respect, the term "executable" means a program file that is in a form that can ultimately be run by the processor. Examples of executable programs can be, for example, a compiled program that can be translated into machine code in a format that can be loaded into a random access portion of the memory and run by the processor, source code that can be expressed in proper format such as object code that is capable of being loaded into a random access portion of the memory and executed by the processor, or source code that can be interpreted by another executable program to generate instructions in a random access portion of the memory to be executed by the processor, etc. An executable program can be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory is defined herein as including both volatile and nonvolatile memory and data storage components. Volatile components are those that do not retain data values upon loss of power. Nonvolatile components are those that retain data upon a loss of power. Thus, the memory can include, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM can include, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device. The memory may also comprise memory present as a subcomponent of the processor, which can include the processor's firmware and internal programming memory.

Also, the processor can represent multiple processors and/or multiple processor cores and the memory can represent multiple memories that operate in parallel processing circuits, respectively. In such a case, the local interface can be an appropriate network that facilitates communication between any two of the multiple processors, between any processor and any of the memories, or between any two of the memories, etc. The local interface can include additional systems designed to coordinate this communication, including, for example, performing load balancing. The processor can be of electrical or of some other available construction.

Although some of the processing systems described herein can be embodied in software or code executed by general purpose hardware as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc.

It should be understood that any logic or application described herein that incorporates software or code can be embodied in any non-transitory computer-readable medium for use by or in connection with an instruction execution system such as, for example, a processor in a computer system or other system. In this sense, the logic can include, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can incorporate any one of many physical media such as, for example, magnetic, optical, or semiconductor media. More specific examples of a suitable computer-readable medium include, but are not limited to, magnetic tapes, magnetic floppy diskettes, magnetic hard drives, memory cards, solid-state drives, USB flash drives, or optical discs. Also, the computer-readable medium can be a random access memory (RAM) including, for example, static random access memory (SRAM) and dynamic random access memory (DRAM), or magnetic random access memory (MRAM). In addition, the computer-readable medium can be a read-only memory (ROM), a programmable read-only memory (PROM), an erasable programmable read-only memory (EPROM), an electrically erasable programmable read-only memory (EEPROM), or other type of memory device.

Further, any logic or application described herein can be implemented and structured in a variety of ways. For example, one or more applications described can be implemented as modules or components of a single application. Further, one or more applications described herein can be executed in shared or separate computing devices or a combination thereof. For example, a plurality of the applications described herein can execute in the same computing device 515, or in multiple computing devices in the same computing environment. Additionally, it is understood that terms such as "application," "service," "system," "engine," "module," and so on may be interchangeable and are not intended to be limiting.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Further, the invention can be characterized by certain aspects as noted below:

1. A near-infrared spectroscopy (NIRS) system (100) can include a substrate (110); a first light source bank (120) capable of emitting a first set of wavelengths of red or near-infrared light, the first light source bank (120) mounted on the substrate (110); an optical detector (140) capable of detecting the first set of wavelengths, the optical detector (140) mounted on the substrate (110) at a first distance from the first light source bank (120); a processor in electronic communication with at least one of the first light source bank (120) and the optical detector (140), the processor is mounted on the substrate (110). A memory device can be in electronic communication with the processor, the memory device mounted on the substrate and the memory device is non-transient; and a battery (150) in electronic communication with at least one of the first light source bank (120), the optical detector (140), the processor, and the memory device; and program instructions stored on the memory device that, when executed, direct the processor to perform certain tasks:

select, based on an input parameter, the first set of wavelengths;

select, based on the input parameter, the first distance from the first light source bank (120);

process a signal from the optical detector (140) to calculate an oxygenation level;

compare the oxygenation level to a predetermined threshold; and at least one of:

filter the signal from the optical detector (140);

activate a feedback device when the oxygenation level is below the predetermined threshold; and store at least one of the signal and the oxygenation level on the memory device, 2. The system (100) of aspect 1, further includes:

a second light source bank (130) capable of emitting a second set of wavelengths of red or near-infrared light, the second light source bank (130) mounted on the substrate (110);

wherein the optical detector (140) is capable of detecting the first set of wavelengths and the second set of wavelengths, the optical detector (140) mounted on the substrate (110) at the first distance from the first light source bank (120) and at a second distance from the second light source bank (130); wherein the processor is in electronic communication with at least one of the first light source bank (120), the second light source bank (130), and the optical detector (140);

wherein the battery (150) is in electronic communication with at least one of the first light source bank (120), the second light source bank (130), the optical detector (140), the processor, and the memory device; and wherein the program instructions, when executed, direct the processor to:

select, based on the input parameter, at least one of the first set of wavelengths and the second set of wavelengths; and select, based on the input parameter, at least one of the first distance from the first light source bank (120) and the second distance from the second light source bank (130).

3. The system (100) of aspect 1, wherein more than one optical detector is capable of detecting wavelengths from more than one light source bank.

4. The system (100) of aspect 1, wherein the substrate (110) is a flexible substrate.

5. The system (100) of aspect 4, wherein the flexible substrate is configured to conform to at least a portion of a skull of a mammal.

6. The system (100) of aspect 1, wherein the substrate (110) comprises at least one rigid portion (170) and at least one flexible portion (180).

7. The system (100) of aspect 6, wherein the substrate (110) is configured to conform to at least a portion of a skull of a mammal.

8. The system (100) of aspect 2, wherein the battery (150) is in electronic communication with the at least one of the first light source bank (120), the second light source bank (130), the optical detector (140), the processor, and the memory device, via a connector (160).

9. The system (100) of aspect 2, wherein a first assembly (190) comprises the substrate (110), the first light source bank (120), the second light source bank (130), the optical detector (140), the processor, and the memory device; and wherein a second assembly (195) comprises the battery (150).

10. The system (100) of aspect 1, wherein the predetermined threshold of the oxygenation level is from about 50% oxygen to about 100% oxygen.

11. The system (100) of aspect 1, wherein the feedback device is selected from the group consisting of a display, an audible feedback device, a haptic feedback device, a color-based feedback device, a fragrance-based feedback device, a tactile feedback device, and combinations thereof.

12. The system (100) of aspect 2, wherein the optical detector (140) is movably mounted to the substrate (110), and wherein selecting, based on the input parameter, at least one of the first distance from the first light source bank (120) and the second distance from the second light source bank (130), further comprises instructing the optical detector (140) to move to at least one of the first distance and the second distance.

13. The system (100) of aspect 1, further comprising a shielding device (115) disposed over at least a portion of the substrate (110).

14. The system (100) of aspect 13, wherein the shielding device (115) is selected from the group consisting of a metal shield, a layer of reflective paint, a synthetic polymer enclosure, a layer of darkened adhesive, and combinations thereof.

15. The system (100) of aspect 1, further comprising an accelerometer mounted on the substrate (110).

16. The system (100) of aspect 15, wherein the accelerometer is capable of detecting a change in velocity up to about 200G.

17. The system (100) of aspect 16, wherein the program instructions further direct the processor to modify the feedback device when the change in velocity differs from a threshold for a predetermined period of time.

18. The system (100) of aspect 1, wherein the predetermined threshold comprises a first predetermined threshold and a second predetermined threshold.

19. The system (100) of aspect 18, further comprising an inflatable wearable device, wherein the program instructions further direct at least one portion of the wearable device to adjust an inflation level of the inflatable wearable device when the oxygenation level is below the first predetermined threshold, or when the oxygenation level is above the second predetermined threshold.

20. The system (100) of aspect 18, further comprising an inflatable wearable device, wherein the program instructions further direct at least one portion of the wearable device to adjust an inflation level of the inflatable wearable device when the oxygenation level is above the first predetermined threshold, or when the oxygenation level is below the second predetermined threshold.

21. A method of detecting an oxygenation level, the method comprising:

mounting the system (100) of aspect 1 in a wearable article;

placing the wearable article on a body of a user;

executing the program instructions for a period of time to calculate a baseline oxygenation level;

regularly executing the program instructions to calculate the oxygenation level; and activating the feedback device when the oxygenation level is different from the predetermined threshold.

22. The method of aspect 21, wherein the predetermined threshold comprises a first predetermined threshold and a second predetermined threshold.

23. The method of aspect 22, wherein the first predetermined threshold is from about 5% to about 25% below the baseline oxygenation level.

24. The method of aspect 22, wherein the second predetermined threshold is from about 5% to about 25% above the baseline oxygenation level.

25. The method of aspect 22, wherein the system (100) further comprises an oxygenation device, and wherein the method further comprises adjusting an output level of the oxygenation device when the oxygenation level is below the first predetermined threshold, or when the oxygenation level is above the second predetermined threshold.

26. The method of aspect 22, wherein the system (100) further comprises an oxygenation device, and wherein the method further comprises maintaining an output level of the oxygenation device when the oxygenation level is above the first predetermined threshold, or when the oxygenation level is below the second predetermined threshold.

27. The method of aspect 25, wherein the oxygenation device is selected from the group consisting of an oxygen tank, an extracorporeal membrane oxygenation (ECMO) device, and a combination thereof.

28. The method of aspect 22, wherein the wearable article is inflatable, and wherein the method further comprises increasing an inflation level of the wearable article when the oxygenation level is below the first predetermined threshold, or when the oxygenation level is above the second predetermined threshold.

29. The method of aspect 22, wherein the wearable article is inflatable, and wherein the method further comprises at maintaining an inflation level of the wearable article when the oxygenation level is above the first predetermined threshold, or when the oxygenation level is below the second predetermined threshold.

30. The method of aspect 22, comprising activating the feedback device when the oxygenation level is below the first predetermined threshold, or when the oxygenation level is above the second predetermined threshold.

31. The method of aspect 22, comprising deactivating the feedback device when the oxygenation level is above the first predetermined threshold, or when the oxygenation level is below the second predetermined threshold.

32. The method of aspect 21, wherein the wearable article is selected from the group consisting of a helmet, a hat, a body suit, a leg covering, a torso covering, an arm covering, a foot covering, and combinations thereof.

33. The system (100) of aspect 1, further comprising an external computing device comprising a memory and a computer processor, the external computing device connected to at least a portion of at least one of the processor and the memory device via a connection, wherein at least a portion of the program instructions is also stored on the external computing device.

34. The system (100) of aspect 33, wherein the connection is selected from the group consisting of a wireless connection, a wired connection, a Bluetooth connection, a near-field communication (NFC) connection, a radio frequency identification (RFID) connection, and combinations thereof.

35. The system (100) of aspect 1, wherein the substrate (110) is a rigid substrate.

36. The system (100) of aspect 1, wherein each wavelength within the first set of wavelengths is from about 660 nm to about 940 nm.

37. The system (100) of aspect 1, wherein each wavelength within the first set of wavelengths is greater than about 805 nm.

38. The system (100) of aspect 2, wherein each wavelength within the second set of wavelengths is from about 660 nm to about 940 nm.

39. The system (100) of aspect 2, wherein each wavelength within the second set of wavelengths is less than about 805 nm.

40. The system (100) of aspect 1, wherein the first distance from the first light source bank (120) is from about 0.8 cm to about 4.5 cm.

41. The system (100) of aspect 1, wherein the first distance from the first light source bank (120) is about 4 cm.

42. The system (100) of aspect 2, wherein the second distance from the second light source bank (130) is from about 0.8 cm to about 4.5 cm.

43. The system (100) of aspect 2, wherein the second distance from the second light source bank (130) is about 1.5 cm.

What is claimed is:

1. A near-infrared spectroscopy (NIRS) system comprising:
   a substrate;
   a first light source bank capable of emitting a first set of wavelengths of red or near-infrared light, the first light source bank mounted on the substrate;
   an optical detector capable of detecting the first set of wavelengths, the optical detector mounted on the substrate at a first distance from the first light source bank;
   a processor in electronic communication with at least one of the first light source bank and the optical detector, the processor mounted on the substrate;
   a memory device in electronic communication with the processor, the memory device mounted on the substrate, wherein the memory device is non-transient; and
   a battery in electronic communication with at least one of the first light source bank, the optical detector, the processor, and the memory device; and
   program instructions stored on the memory device that, when executed, direct the processor to:
      select, based on an input parameter, the first set of wavelengths;
      select, based on the input parameter, the first distance from the first light source bank;
      process a signal from the optical detector to calculate an oxygenation level;
      compare the oxygenation level to a predetermined threshold; and
      at least one of:
         filter the signal from the optical detector;
         activate a feedback device when the oxygenation level is below the predetermined threshold; and
         store at least one of the signal and the oxygenation level on the memory device.

2. The system of claim 1, further comprising:
   a second light source bank capable of emitting a second set of wavelengths of red or near-infrared light, the second light source bank mounted on the substrate;
   wherein the optical detector is capable of detecting the first set of wavelengths and the second set of wavelengths, the optical detector mounted on the substrate at the first distance from the first light source bank and at a second distance from the second light source bank;
   wherein the processor is in electronic communication with at least one of the first light source bank, the second light source bank, and the optical detector;
   wherein the battery is in electronic communication with at least one of the first light source bank, the second light source bank, the optical detector, the processor, and the memory device; and
   wherein the program instructions, when executed, direct the processor to:
      select, based on the input parameter, at least one of the first set of wavelengths and the second set of wavelengths; and
      select, based on the input parameter, at least one of the first distance from the first light source bank and the second distance from the second light source bank.

3. The system of claim 2, wherein the battery is in electronic communication with the at least one of the first light source bank, the second light source bank, the optical detector, the processor, and the memory device, via a connector.

4. The system of claim 2, wherein a first assembly comprises the substrate, the first light source bank, the second light source bank, the optical detector, the processor, and the memory device; and wherein a second assembly comprises the battery.

5. The system of claim 2, wherein the optical detector is movably mounted to the substrate, and wherein selecting, based on the input parameter, at least one of the first distance from the first light source bank and the second distance from the second light source bank, further comprises instructing the optical detector to move to at least one of the first distance and the second distance.

6. The system of claim 1, wherein more than one optical detector is capable of detecting wavelengths from more than one light source bank.

7. The system of claim 1, wherein the substrate is a flexible substrate.

8. The system of claim 7, wherein the flexible substrate is configured to conform to at least a portion of a skull of a mammal.

9. The system of claim 1, wherein the substrate comprises at least one rigid portion and at least one flexible portion.

10. The system of claim 9, wherein the substrate is configured to conform to at least a portion of a skull of a mammal.

11. The system of claim 1, wherein the predetermined threshold of the oxygenation level is from about 50% oxygen to about 100% oxygen.

12. The system of claim 1, further comprising a shielding device disposed over at least a portion of the substrate.

13. The system of claim 1, further comprising an accelerometer mounted on the substrate.

14. The system of claim 13, wherein the program instructions further direct the processor to modify the feedback device when the change in velocity differs from a threshold for a predetermined period of time.

15. The system of claim 1, wherein the predetermined threshold comprises a first predetermined threshold and a second predetermined threshold.

16. The system of claim 15, further comprising an inflatable wearable device, wherein the program instructions further direct at least one portion of the wearable device to adjust an inflation level of the inflatable wearable device when the oxygenation level is different than the first predetermined threshold, or when the oxygenation level is different than the second predetermined threshold.

17. The system of claim 1, wherein the substrate is a rigid substrate.

18. The system of claim 1, wherein each wavelength within the first set of wavelengths is from about 660 nm to about 940 nm.

19. The system of claim 1, wherein the first distance from the first light source bank is from about 0.8 cm to about 4.5 cm.

* * * * *